(12) United States Patent
Hegde et al.

(10) Patent No.: US 8,588,884 B2
(45) Date of Patent: Nov. 19, 2013

(54) MICRONEEDLE ELECTRODE

(75) Inventors: Anant V. Hegde, Hayward, CA (US);
Amit Rajguru, Lafayette, CA (US);
Daniel Rogers Burnett, San Francisco, CA (US); Christopher Hermanson, Santa Cruz, CA (US)

(73) Assignee: EMKinetics, Inc., San Francisco, CA (US)

( * ) Notice: Subject to any disclaimer, the term of this patent is extended or adjusted under 35 U.S.C. 154(b) by 277 days.

(21) Appl. No.: 12/790,619

(22) Filed: May 28, 2010

(65) Prior Publication Data

US 2011/0295100 A1   Dec. 1, 2011

(51) Int. Cl.
| | |
|---|---|
| *A61B 5/0408* | (2006.01) |
| *A61B 5/0416* | (2006.01) |
| *A61B 5/0478* | (2006.01) |
| *A61B 5/0492* | (2006.01) |
| *A61N 1/04* | (2006.01) |

(52) U.S. Cl.
USPC ........... 600/372; 600/373; 600/391; 607/142; 607/149

(58) Field of Classification Search
USPC ............... 600/372, 373, 391; 607/142, 149
See application file for complete search history.

(56) References Cited

U.S. PATENT DOCUMENTS

| | | | |
|---|---|---|---|
| 2,893,392 A | 7/1959 | Wagner et al. | |
| 3,034,507 A | 5/1962 | McConnell et al. | |
| 3,817,254 A | 6/1974 | Maurer | |
| 3,841,305 A | 10/1974 | Hallgren | |
| 4,233,965 A | 11/1980 | Fairbanks | |
| 4,266,533 A | 5/1981 | Ryaby et al. | |
| 4,428,366 A | 1/1984 | Findl et al. | |
| 4,456,012 A | 6/1984 | Lattin | |
| 4,548,208 A | 10/1985 | Niemi | |
| 4,574,809 A | 3/1986 | Talish et al. | |
| 4,784,737 A | 11/1988 | Ray et al. | |
| 4,804,054 A | 2/1989 | Howson et al. | |
| 4,837,049 A | 6/1989 | Byers et al. | |
| 4,915,110 A | 4/1990 | Kitov | |
| 4,940,453 A | 7/1990 | Cadwell | |

(Continued)

FOREIGN PATENT DOCUMENTS

| | | |
|---|---|---|
| GB | 0637560 | 5/1950 |
| GB | 2298370 | 9/1996 |

(Continued)

OTHER PUBLICATIONS

"Bioflex® RX754P , Single Coated Medical Pressure Sensitive Adhesive Tape," *Technical Data*, 2 pages, Dec. 2005.

(Continued)

*Primary Examiner* — Lee S Cohen
(74) *Attorney, Agent, or Firm* — Levine Bagade Han LLP

(57) ABSTRACT

In certain variations, methods, systems and/or devices for enhancing conductivity of an electrical signal through a subject's skin using one or more microneedle electrodes are provided. A microneedle electrode may be applied to the subject's skin by placing the microneedle electrode in direct contact with the subject's skin. The microneedles of the microneedle electrode may be inserted into the skin such that the microneedles pierce stratum corneum of the skin up to or through dermis of the skin. An electrical signal passes or is conducted through or across the microneedle electrode and the subject's skin, where impedance of the microneedle electrode is minimal and greatly reduced compared to existing technologies.

25 Claims, 14 Drawing Sheets

(56) References Cited

U.S. PATENT DOCUMENTS

| | | | |
|---|---|---|---|
| 5,000,178 A | 3/1991 | Griffith | |
| 5,014,699 A | 5/1991 | Pollack et al. | |
| 5,092,835 A | 3/1992 | Schurig et al. | |
| 5,181,902 A | 1/1993 | Erickson et al. | |
| 5,309,909 A * | 5/1994 | Gadsby et al. | 600/386 |
| 5,314,401 A | 5/1994 | Tepper | |
| 5,314,453 A | 5/1994 | Jeutter | |
| 5,401,233 A | 3/1995 | Erickson et al. | |
| 5,449,378 A | 9/1995 | Schouenborg | |
| 5,518,495 A | 5/1996 | Kolt | |
| 5,562,707 A | 10/1996 | Prochazka et al. | |
| 5,690,693 A | 11/1997 | Wang et al. | |
| 5,715,837 A | 2/1998 | Chen | |
| 5,725,471 A | 3/1998 | Davey et al. | |
| 5,749,909 A | 5/1998 | Schroeppel et al. | |
| 5,766,124 A | 6/1998 | Polson | |
| 5,792,187 A | 8/1998 | Adams | |
| 5,792,209 A | 8/1998 | Varner | |
| 5,833,600 A | 11/1998 | Young | |
| 5,857,957 A | 1/1999 | Lin | |
| 5,978,712 A | 11/1999 | Suda et al. | |
| 5,984,854 A | 11/1999 | Ishikawa et al. | |
| 6,009,878 A | 1/2000 | Weijand et al. | |
| 6,024,691 A | 2/2000 | Tepper et al. | |
| 6,029,090 A | 2/2000 | Herbst | |
| 6,032,677 A | 3/2000 | Blechman et al. | |
| 6,066,084 A | 5/2000 | Edrich et al. | |
| 6,086,525 A | 7/2000 | Davey et al. | |
| 6,088,619 A | 7/2000 | Hein et al. | |
| 6,123,658 A | 9/2000 | Schweighofer et al. | |
| 6,143,035 A | 11/2000 | McDowell | |
| 6,155,966 A | 12/2000 | Parker | |
| 6,179,770 B1 | 1/2001 | Mould | |
| 6,190,893 B1 | 2/2001 | Shastri et al. | |
| 6,200,259 B1 | 3/2001 | March | |
| 6,213,933 B1 | 4/2001 | Lin | |
| 6,219,575 B1 | 4/2001 | Nemati | |
| 6,256,533 B1 | 7/2001 | Yuzhakov et al. | |
| 6,261,221 B1 | 7/2001 | Tepper et al. | |
| 6,312,612 B1 | 11/2001 | Sherman et al. | |
| 6,334,856 B1 * | 1/2002 | Allen et al. | 604/191 |
| 6,349,233 B1 | 2/2002 | Adams | |
| 6,379,324 B1 | 4/2002 | Gartstein et al. | |
| 6,440,096 B1 | 8/2002 | Lastovich et al. | |
| 6,443,883 B1 | 9/2002 | Ostrow et al. | |
| 6,451,240 B1 | 9/2002 | Sherman et al. | |
| 6,471,903 B2 | 10/2002 | Sherman et al. | |
| 6,473,652 B1 | 10/2002 | Sarwal et al. | |
| 6,491,620 B1 | 12/2002 | Davey | |
| 6,493,588 B1 | 12/2002 | Malaney et al. | |
| 6,500,110 B1 | 12/2002 | Davey et al. | |
| 6,503,231 B1 | 1/2003 | Prausnitz et al. | |
| 6,511,463 B1 | 1/2003 | Wood et al. | |
| 6,527,694 B1 | 3/2003 | Ishikawa et al. | |
| 6,533,949 B1 | 3/2003 | Yeshurun et al. | |
| 6,537,242 B1 | 3/2003 | Palmer | |
| 6,553,263 B1 | 4/2003 | Meadows et al. | |
| 6,558,361 B1 | 5/2003 | Yeshurun | |
| 6,565,532 B1 | 5/2003 | Yuzhakov et al. | |
| 6,582,393 B2 | 6/2003 | Sage, Jr. | |
| 6,591,124 B2 | 7/2003 | Sherman et al. | |
| 6,595,947 B1 | 7/2003 | Mikszta et al. | |
| 6,603,987 B2 | 8/2003 | Whitson | |
| 6,611,707 B1 | 8/2003 | Prausnitz et al. | |
| 6,622,035 B1 * | 9/2003 | Merilainen et al. | 600/391 |
| 6,623,457 B1 | 9/2003 | Rosenberg | |
| 6,652,443 B1 | 11/2003 | Struppler et al. | |
| 6,652,478 B1 | 11/2003 | Gartstein et al. | |
| 6,654,636 B1 | 11/2003 | Dev et al. | |
| 6,656,147 B1 | 12/2003 | Gertsek et al. | |
| 6,663,556 B2 | 12/2003 | Barker | |
| 6,663,820 B2 | 12/2003 | Arias et al. | |
| 6,671,527 B2 | 12/2003 | Petersson et al. | |
| 6,678,556 B1 | 1/2004 | Nolan et al. | |
| 6,684,106 B2 | 1/2004 | Herbst | |
| 6,689,100 B2 | 2/2004 | Connelly et al. | |
| 6,690,959 B2 * | 2/2004 | Thompson | 600/372 |
| 6,697,669 B2 | 2/2004 | Dev et al. | |
| 6,701,185 B2 | 3/2004 | Burnett et al. | |
| 6,735,474 B1 | 5/2004 | Loeb et al. | |
| 6,743,211 B1 | 6/2004 | Prausnitz et al. | |
| 6,767,341 B2 | 7/2004 | Cho | |
| 6,770,022 B2 | 8/2004 | Mechlenburg et al. | |
| 6,770,480 B1 | 8/2004 | Canham | |
| 6,782,283 B2 * | 8/2004 | Schmidt et al. | 600/372 |
| 6,790,372 B2 | 9/2004 | Roy et al. | |
| 6,808,506 B2 | 10/2004 | Lastovich et al. | |
| 6,835,184 B1 | 12/2004 | Sage et al. | |
| 6,866,659 B2 | 3/2005 | Nemati | |
| 6,881,203 B2 | 4/2005 | Delmore et al. | |
| 6,899,838 B2 | 5/2005 | Lastovich | |
| 6,908,453 B2 | 6/2005 | Fleming et al. | |
| 6,926,660 B2 | 8/2005 | Miller | |
| 6,931,277 B1 | 8/2005 | Yuzhakov et al. | |
| 6,939,311 B2 | 9/2005 | Geiger | |
| 6,941,171 B2 | 9/2005 | Mann et al. | |
| 6,960,193 B2 | 11/2005 | Rosenberg | |
| 6,962,772 B2 | 11/2005 | Liu et al. | |
| 6,972,013 B1 | 12/2005 | Zhang et al. | |
| 6,980,855 B2 | 12/2005 | Cho | |
| 7,013,179 B2 | 3/2006 | Carter et al. | |
| 7,027,478 B2 | 4/2006 | Ackley | |
| 7,045,069 B2 | 5/2006 | Ozeryansky | |
| 7,047,070 B2 | 5/2006 | Wilkinson et al. | |
| 7,048,723 B1 | 5/2006 | Frazier et al. | |
| 7,079,355 B2 | 7/2006 | Hsiao et al. | |
| 7,083,592 B2 | 8/2006 | Lastovich et al. | |
| 7,104,947 B2 | 9/2006 | Riehl | |
| 7,115,108 B2 | 10/2006 | Wilkinson et al. | |
| 7,117,034 B2 | 10/2006 | Kronberg | |
| 7,130,696 B2 | 10/2006 | Carter et al. | |
| 7,132,054 B1 | 11/2006 | Kravitz et al. | |
| 7,153,256 B2 | 12/2006 | Riehl et al. | |
| 7,187,976 B2 | 3/2007 | Duncan et al. | |
| 7,226,439 B2 | 6/2007 | Prausnitz et al. | |
| 7,262,068 B2 | 8/2007 | Roy et al. | |
| 7,273,474 B2 | 9/2007 | Chang et al. | |
| 7,285,113 B2 | 10/2007 | Yeshurun | |
| 7,315,758 B2 | 1/2008 | Kwiatkowski et al. | |
| 7,316,665 B2 | 1/2008 | Laurent et al. | |
| 7,320,664 B2 | 1/2008 | Riehl et al. | |
| 7,332,197 B2 | 2/2008 | Wood et al. | |
| 7,332,339 B2 | 2/2008 | Canham | |
| 7,344,499 B1 | 3/2008 | Prausnitz et al. | |
| 7,367,936 B2 | 5/2008 | Myers et al. | |
| D571,920 S | 6/2008 | Juliana et al. | |
| 7,396,326 B2 | 7/2008 | Ghiron et al. | |
| 7,410,476 B2 | 8/2008 | Wilkinson et al. | |
| 7,415,299 B2 | 8/2008 | Zimmermann et al. | |
| 7,416,541 B2 | 8/2008 | Yuzhakov et al. | |
| 7,429,333 B2 | 9/2008 | Chiou et al. | |
| 7,473,244 B2 | 1/2009 | Frazier et al. | |
| 7,481,337 B2 | 1/2009 | Luharuka et al. | |
| 7,497,980 B2 | 3/2009 | Xu et al. | |
| 7,500,911 B2 | 3/2009 | Johnson et al. | |
| 7,520,848 B2 | 4/2009 | Schneider et al. | |
| 7,522,061 B2 | 4/2009 | Rondoni et al. | |
| 7,530,968 B2 | 5/2009 | Gonnelli | |
| 7,536,226 B2 | 5/2009 | Williams et al. | |
| 7,556,615 B2 | 7/2009 | Pettis et al. | |
| 7,556,821 B2 | 7/2009 | Ameri et al. | |
| 7,560,036 B2 | 7/2009 | Golubovic-Liakopoulos et al. | |
| 7,570,992 B2 | 8/2009 | Nolan et al. | |
| 7,572,405 B2 | 8/2009 | Sherman et al. | |
| 7,574,256 B2 | 8/2009 | Carter | |
| 7,578,954 B2 | 8/2009 | Gartstein et al. | |
| 7,582,069 B2 | 9/2009 | Laurent et al. | |
| 7,588,552 B2 | 9/2009 | Yeshurun et al. | |
| 7,591,806 B2 | 9/2009 | Xu | |
| 7,627,938 B2 | 12/2009 | Kim et al. | |
| 7,647,112 B2 | 1/2010 | Tracey et al. | |
| 7,648,484 B2 | 1/2010 | Yeshurun et al. | |
| 7,651,946 B2 | 1/2010 | Wilke et al. | |
| 7,658,728 B2 | 2/2010 | Yuzhakov | |

(56) References Cited

U.S. PATENT DOCUMENTS

| | | | |
|---|---|---|---|
| 7,941,201 B2* | 5/2011 | Chiou et al. | 600/373 |
| 8,430,805 B2 | 4/2013 | Burnett et al. | |
| 8,435,166 B2 | 5/2013 | Burnett et al. | |
| 2002/0028991 A1 | 3/2002 | Thompson | |
| 2002/0082465 A1 | 6/2002 | Bashford et al. | |
| 2002/0099323 A1 | 7/2002 | Dev et al. | |
| 2002/0111777 A1 | 8/2002 | David | |
| 2002/0133129 A1 | 9/2002 | Arias et al. | |
| 2002/0183804 A1 | 12/2002 | Malaney et al. | |
| 2003/0028072 A1 | 2/2003 | Fischell et al. | |
| 2003/0144625 A1 | 7/2003 | Sherman et al. | |
| 2003/0158583 A1 | 8/2003 | Burnett et al. | |
| 2003/0158585 A1 | 8/2003 | Burnett | |
| 2003/0216729 A1 | 11/2003 | Marchitto et al. | |
| 2003/0217754 A1 | 11/2003 | Thomas et al. | |
| 2004/0054393 A1* | 3/2004 | Stemme et al. | 607/149 |
| 2004/0082875 A1* | 4/2004 | Donoghue et al. | 600/544 |
| 2004/0092860 A1 | 5/2004 | Dev et al. | |
| 2004/0111139 A1 | 6/2004 | McCreery | |
| 2004/0122787 A1 | 6/2004 | Avanash et al. | |
| 2004/0138517 A1 | 7/2004 | Osorio et al. | |
| 2004/0146611 A1 | 7/2004 | Arias et al. | |
| 2004/0147964 A1 | 7/2004 | Nolan et al. | |
| 2004/0173220 A1 | 9/2004 | Harry et al. | |
| 2004/0210254 A1 | 10/2004 | Burnett et al. | |
| 2004/0210282 A1 | 10/2004 | Flock et al. | |
| 2005/0021104 A1 | 1/2005 | Dilorenzo | |
| 2005/0029223 A1 | 2/2005 | Yeshurun | |
| 2005/0099290 A1 | 5/2005 | Govari | |
| 2005/0143783 A1 | 6/2005 | Boveja et al. | |
| 2005/0143789 A1 | 6/2005 | Whitehurst et al. | |
| 2005/0171576 A1 | 8/2005 | Williams et al. | |
| 2005/0277998 A1 | 12/2005 | Tracey et al. | |
| 2005/0283202 A1 | 12/2005 | Gellman | |
| 2006/0004244 A1 | 1/2006 | Phillips et al. | |
| 2006/0016452 A1 | 1/2006 | Goetz et al. | |
| 2006/0047316 A1 | 3/2006 | Fischell et al. | |
| 2006/0049957 A1 | 3/2006 | Surgenor et al. | |
| 2006/0052839 A1 | 3/2006 | Kim et al. | |
| 2006/0084938 A1 | 4/2006 | Zhang et al. | |
| 2006/0122454 A1 | 6/2006 | Riehl et al. | |
| 2006/0122660 A1 | 6/2006 | Boveja et al. | |
| 2006/0161039 A1 | 7/2006 | Juliana et al. | |
| 2006/0173261 A1* | 8/2006 | Kall et al. | 600/372 |
| 2006/0199159 A1 | 9/2006 | Ghiron et al. | |
| 2006/0276702 A1 | 12/2006 | McGinnis | |
| 2007/0021803 A1 | 1/2007 | Deem et al. | |
| 2007/0027353 A1 | 2/2007 | Ghiron et al. | |
| 2007/0027354 A1 | 2/2007 | Riehl et al. | |
| 2007/0027355 A1 | 2/2007 | Riehl et al. | |
| 2007/0142885 A1 | 6/2007 | Hantash et al. | |
| 2007/0208212 A1 | 9/2007 | Dilorenzo | |
| 2007/0250162 A1 | 10/2007 | Royalty | |
| 2007/0265489 A1 | 11/2007 | Fowler et al. | |
| 2007/0276318 A1 | 11/2007 | Henley | |
| 2007/0282246 A1 | 12/2007 | Henley | |
| 2008/0004484 A1 | 1/2008 | Wieraszko et al. | |
| 2008/0063866 A1 | 3/2008 | Allen et al. | |
| 2008/0114199 A1 | 5/2008 | Riehl et al. | |
| 2008/0177128 A1 | 7/2008 | Riehl et al. | |
| 2008/0183070 A1 | 7/2008 | Unal et al. | |
| 2008/0200748 A1 | 8/2008 | Testani et al. | |
| 2008/0224808 A1 | 9/2008 | Ghiron et al. | |
| 2008/0262287 A1 | 10/2008 | Dussau | |
| 2008/0288035 A1 | 11/2008 | Gill et al. | |
| 2008/0306325 A1 | 12/2008 | Burnett et al. | |
| 2008/0312725 A1 | 12/2008 | Penner | |
| 2009/0073991 A1 | 3/2009 | Landrum et al. | |
| 2009/0076336 A1 | 3/2009 | Mazar et al. | |
| 2009/0076340 A1 | 3/2009 | Libbus et al. | |
| 2009/0076344 A1 | 3/2009 | Libbus et al. | |
| 2009/0076345 A1 | 3/2009 | Manicka et al. | |
| 2009/0076363 A1 | 3/2009 | Bly et al. | |
| 2009/0076364 A1 | 3/2009 | Libbus et al. | |
| 2009/0076397 A1 | 3/2009 | Libbus et al. | |
| 2009/0076410 A1 | 3/2009 | Libbus et al. | |
| 2009/0076559 A1 | 3/2009 | Libbus et al. | |
| 2009/0076565 A1 | 3/2009 | Surwit | |
| 2009/0118777 A1 | 5/2009 | Iki et al. | |
| 2009/0132018 A1 | 5/2009 | DiUbaldi et al. | |
| 2009/0162570 A1 | 6/2009 | Swenberg et al. | |
| 2009/0171236 A1 | 7/2009 | Davies | |
| 2009/0227829 A1 | 9/2009 | Burnett et al. | |
| 2009/0227831 A1 | 9/2009 | Burnett et al. | |
| 2009/0234179 A1 | 9/2009 | Burnett et al. | |
| 2009/0234410 A1 | 9/2009 | Libbus et al. | |
| 2009/0264792 A1 | 10/2009 | Mazar | |
| 2009/0292194 A1 | 11/2009 | Libbus et al. | |
| 2010/0022864 A1* | 1/2010 | Cordero et al. | 600/372 |
| 2010/0049021 A1 | 2/2010 | Jina et al. | |
| 2010/0056881 A1 | 3/2010 | Libbus et al. | |
| 2010/0160712 A1 | 6/2010 | Burnett et al. | |
| 2010/0161005 A1 | 6/2010 | Wahlgren et al. | |
| 2010/0168501 A1 | 7/2010 | Burnett et al. | |
| 2010/0204538 A1 | 8/2010 | Burnett et al. | |
| 2010/0222629 A1 | 9/2010 | Burnett et al. | |
| 2010/0222630 A1 | 9/2010 | Mangrum et al. | |
| 2011/0021863 A1 | 1/2011 | Burnett et al. | |
| 2013/0072746 A1 | 3/2013 | Burnett et al. | |

FOREIGN PATENT DOCUMENTS

| | | |
|---|---|---|
| GB | 2336544 | 10/1999 |
| JP | 2000-254239 | 9/2000 |
| WO | WO 03/070317 | 8/2003 |
| WO | WO 2008/032279 | 3/2008 |
| WO | WO 2008/042902 | 4/2008 |
| WO | WO 2008/115426 | 9/2008 |
| WO | WO 2011/011748 | 1/2011 |
| WO | WO 2011/011749 | 1/2011 |
| WO | WO 2011/053607 | 5/2011 |
| WO | WO 2011/053661 | 5/2011 |
| WO | WO 2011/150332 | 12/2011 |
| WO | WO 2012/040243 | 3/2012 |

OTHER PUBLICATIONS

3M Corporation, 3M™ XYZ/Isotropic Electrically Conductive Adhesive Transfer Tape 9707, *3M Electronics Markets Materials Division*, 60-5002-0350-4, 8 pages, 2004, 3M.

Aaron, Roy K. et al., "Therapeutic Effects of Electromagnetic Fields in the Stimulation of Connective Tissue Repair," *Journal of Cellular Biography*, 52(1):42-6, May 1993, Wiley-Liss, Inc.

AmGel Technologies, "AG603 Sensing Gel, Sensing Gel Designed for ECG Applications," AG603-3/10, 1 page, 2010.

AmGel Technologies, "AG702 Stimulating Gel, Stimulating Gel Designed for carbon film," AG702-02/06, 1 page, 2006.

AmGel Technologies, "AG902-184/229 Grounding Gel, Grounding Gel Designed for Electrosurgical Pads," AG902 Series, 1 page, 2010.

AmGel Technologies, "Release Films," 1 Page, Jul. 25, 2006, Revision 1.

Australian Patent Application No. 2007303223 filed Oct. 2, 2007 in the name of EMKinetics, Inc., Office Action mailed Sep. 7, 2010.

Balmaseda, Marion T. Jr., et al., "Burns in Functional Electric Stimulation: Two Case Reports," *Archives of Physical Medicine and Rehabilitation*, vol. 38., pp. 452-453, Jul. 1987.

Biowave Corporation, "510(k) Summary for the Biowave Deepwave Neuromodulation Pain Therapy Device," 6 pages, Appendix B, Dec. 13, 2005.

Biowave Corporation, "510(k) Summary for the Biowave Deepwave Neuromodulation Pain Therapy Device," 7 pages, Appendix E, Aug. 15, 2006.

Biowave Corporation, "Percutaneous Neuromodulation Pain Therapy System," *deepwave*, RevB/080926, 2008.

BlueCross BlueShield of Kansas City, "Percutaneous Electrical Nerve Stimulation (PENS) and Percutaneous Neuromodulation Therapy (PNT)," 7 pages, 1988.

Bodhale, D.W. et al., "Design, fabrication and analysis of silicon microneedles for transdermal drug delivery applications," *Proceedings of the 3rd International Conference on the Development of BME in Vietnam*, pp. 84-88, Jan. 11-14, 2010.

(56) References Cited

OTHER PUBLICATIONS

Bruce, C.J. et al., "Intracardiac Echocardiography," *European Journal Echocardiography*, vol. 2, pp. 234-244, 2001, The European Society of Cardiology.

Cabodevila, G. et al., "An overview on drug delivery using microneedles", *Institute FEMTO-ST, Dept LPMO*, 24 pages, Oct. 2005, Workshop Micro Dosing Systems.

Certified Pulsed Signal Therapy Centers, http://www.certifiedpst.com, 10 pages.

Choi, S. et al., "Microneedle Electrode Array for Electroporation of Skin for Gene Therapy," 2 pages, 2005, Controlled Release Society 32nd Annual Meeting and Exposition Transactions.

Curley, S. et al., "Radiofrequency Ablation of Unresectable Primary and Metastatic Hepatic Malignancies," *Annals of Surgery*, vol. 230(1):1-8, 1999 Lippincott Williams & Wilkins, Inc.

CystoMedix, Inc., "Percutaneous Tibial Nerve Stimulation via Urgent ® PC Neuromodulation System—An Emerging Technology for managing Overactive Bladder," *Business Briefing: Global Surgery*, 6 pages, 2004.

EBI, L.P., EBI Bone Healing System, http://www.ebimedical.com/products/fracture/bonehealing.html, 5 pages.

Fallon Community Health Plan, "Spinal Cord Stimulation," 4 pages, 2006.

Grundfest H. et al., "Stainless Steel Micro-Needle Electrodes Made by Electrolytic Pointing," *Review of Scientific Instruments*, vol. 21(4):2 pages, 1950, American Institute of Physics.

Harvinder S. Gill et al., "Effect of microneedle design on pain in human subjects," *NIH Public Access Author Manuscript*, 24(7): 585-594, Sep. 2008, Clinical Journal of Pain.

Huber, D.E. et al., "Popliteal Vein Compression Under General Anaesthesia," *European Journal of Vascular and Endovascular Surgery*, vol. 37, pp. 464-469, 2009, Elsevier Ltd.

International Patent Application No. PCT/US2007/080196 in the name of Emkinetics, Inc. filed Oct. 2, 2007, International Search Report and Written Opinion mailed Apr. 24, 2008.

International Patent Application No. PCT/US2010/043142 in the name of Emkinetics, Inc. filed Jul. 23, 2010, International Search Report and Written Opinion mailed Sep. 24, 2010.

International Patent Application No. PCT/US2010/043143 in the name of Emkinetics, Inc. filed Jul. 23, 2010, International Search Report and Written Opinion mailed Sep. 15, 2010.

International Patent Application No. PCT/US2010/054167 in the name of Emkinetics, Inc. filed Oct. 26, 2010, International Search Report and Written Opinion mailed Dec. 23, 2010.

International Patent Application No. PCT/US2010/054353 in the name of Emkinetics, Inc. filed Oct. 27, 2010, International Search Report and Written Opinion mailed Dec. 28, 2010.

Isseroff, Roslyn R. et al., "Beta Adrenergic Receptor (βAR) Signaling as a novel target for optimizing skin wound healing", 5 pages.

Jacobson, Jerry I. et al., "Low-Amplitude, Extremely Low Frequency Magnetic Fields for the Treatment of Osteoarthritic Knees: A Double-Blind Clinical Study," *Electromagnetic Fields and Human Health. Fundamental and Applied Research*, pp. 363-364, Sep. 17-24, 2002, Proceedings of the Third International Conference.

Jasper, H. et al., "Unipolar Electromyograms of Normal and Denervated Human Muscle," pp. 231-244, Oct. 12, 1948, Department of Neurology and Neurosurgery, McGill University, and Montreal Neurological Institute.

Kravitz, S. et al., Microneedles for In-Situ/In-vivo Electrochemical Sensor Applications, 1 page, Sandia National Laboratories.

Kurtzke, John F., "Epidemiology of Spinal Cord Injury," *IV Panamerican Congress of Neurology*, 18(2-3): 157-90, 93, 1975.

Lin et al., "Magnetic Stimulation of the Bladder in Dogs," AAEM Annual Meeting 1993, *Muscle & Nerve*, Oct. 1993 (Abstract).

Luttge, R. "Microneedle array electrode for human EEG recording," IFMBE Proceedings 22, pp. 1246-1249, 2008, Springer-Verlag Berlin Heidelberg 2009.

Maass et al., "Contactless Nerve Stimulation and Signal Detection by Inductive Transducer," *Symposium on Application of Magnetism in Bioengineering*, 1969.

McFarlane, J.P. et al., "Acute Suppression of Idiopathic Detrusor Instability with Magnetic Stimulation of the Sacral Nerve Roots," *British Journal of Urology*, 80(5):734-41, Nov. 1997.

Morrison, P.R. et al., "Radiofrequency Ablation of Thoracic Lesions: Part I, Experiments in the Normal Porcine Thorax," *American Journal of Roentgenology*, 2005;184:375-380, Feb. 2005, American Roentgen Ray Society.

NeuroStar TMS Therapy, NeuroStar TMS Therapy® Recipient of Medical Design Excellence Award, *PRNewswire*, 3 pages, Apr. 2009.

Newmark, Inc., "Standard Products, Highest Quality Components, Designed & Produced Exclusively for Electrode Manufacturers," *Innovation by Design Newmark*, 2 pages, www.newmarkine.com/std_prods.htm, printed on May 3, 2010.

Noble, J.H. et al., "Automatic segmentation of the facial nerve and chorda tympani in CT images using spatially dependent features values", Medical Phsysics, vol. 35(12), pp. 5375-5384, Dec. 2008, American Association Physical Medicine.

Patel, G. et al., "Microneedles: The option for painless delivery," www.pharmainfo.net/reviews/microneedles-option-painless-delivery, 6 pages, printed on Sep. 9, 2008.

*PubMed, U.S. National Library of Medicine National Institutes of Health*, microneedle array electrode—Pub Med results, www.ncbi.nlm.nig.gov/sites/entrez, 2 pages, Search performed on Apr. 22, 2010.

*PubMed, U.S. National Library of Medicine National Institutes of Health*, microneedle electrode—Pub Med results, www.ncbi.nlm.nig.gov/sites/entrez, 7 pages, Search performed on Apr. 22, 2010.

Schaefer, O. et al., "CT-guided radiofrequency ablation of a bronchogenic carcinoma," *The British Journal of Radiology*, 76 (2003), pp. 268-270, 2003, The British Institute of Radiology.

Shafik, Ahmed, "Magnetic Stimulation: A Novel Method for Inducing Evacuation of the Neuropathic Rectum and Urinary Bladder in a Canine Model," *Urology* 54(2):368-372, Aug. 1999.

Sheridan, MT. et al., "Pretreatment apoptosis in carcinoma of the cervix correlates with changes in tumour oxygenation during radiotherapy," *British Journal of Cancer*, 82(6):1177-1182, 2000 Cancer Research Campaign.

Sivagangabalan, G. et al., "Comparison of Electroanatomic Contact and Noncontact Mapping of Ventricular Scar in a Postinfarct Ovine Model With Intramural Needle Electrode Recording and Histological Validation," *Circulation: Arrhythmia and Electrophysiology, Journal of the American Heart Association*, vol. 1:363-369, 2008, American Heart Association.

Solbiati, L. et al., "Percutaneous US-guided Radio-Frequency Tissue Ablation of Liver Metastases: Treatment and Follow-up in 16 Patients," *Radiology*, 202(1):195-203, 1997 L.S. RSNA.

The Magstim Company Ltd, "Air Film Coil," *Magstim*, 4 pages, 2007.

Thon, W.F. et al., "Neuromodulation of voiding dysfunction and pelvic pain," *World Journal of Urology*, vol. 9: pp. 138-141, 1991, Springer-Verlag.

Trock, David H., "Electromagnetic Fields and Magnets Investigational Treatment for Musculoskeletal Disorders," *Rheumatic Diseases Clinics of North America*, vol. 26, No. 1., Feb. 2000.

Trock, David H., et al., "The Effect of Pulsed Electromagnetic Fields in the Treatment of Osteoarthritis of the Knee and Cervical Spine. Report of Randomized, Double Blind, Placebo Controlled Trials," *The Journal of Rheumatology*, 1903-1911, 1994.

Tyco Adhesives, "2932 Designed Adhesives," *Specialty Tape Group*, 1 page.

U.S. Appl. No. 12/815,348, filed Jun. 14, 2010 in the name of Reydel et al., non-final Office Action dated Feb. 14, 2011.

U.S. Appl. No. 10/077,434, filed Feb. 19, 2002 in the name of Burnett et al., non-final Office Action mailed Jul. 2, 2003.

U.S. Appl. No. 10/077,434, filed Feb. 19, 2002 in the name of Burnett et al., Notice of Allowance mailed Oct. 17, 2003.

U.S. Appl. No. 11/332,797, filed Jan. 27, 2006 in the name of Mangrum et al., final Office Action mailed Jul. 27, 2009.

U.S. Appl. No. 11/866,329, filed Oct. 2, 2007 in the name of Burnett et al., final Office Action mailed Mar. 16, 2010.

U.S. Appl. No. 11/866,329, filed Oct. 2, 2007 in the name of Burnett et al., non-final Office Action mailed Jun. 10, 2009.

(56) References Cited

OTHER PUBLICATIONS

U.S. Appl. No. 12/469,365, filed May 20, 2009 in the name of Mangrum et al., non-final Office Action mailed Aug. 27, 2010.

U.S. Appl. No. 12/695,087, filed Jan. 27, 2010 in the name of Mangrum et al., non-final Office Action mailed Dec. 23, 2010.

vanSonnenberg, E. et al., "Radiofrequency Ablation of Thoracic Lesions: Part 2, Initial Clinical Experience—Technical and Multidisciplinary Considerations in 30 Patients," *American Journal of Roentgenology*, 2005;184:381-390, Feb. 2005, American Roentgen Ray Society.

Wanich, T. et al, A Randomized Placebo-Controlled Study to Determine Safety and Efficacy In Terms of Pain Reduction, Increased Range of Motion, and Reduced Pain Medications, for a Novel Percutaneous Neuromodulation Pain Therapy Device ("Deepwave®") Following Post-Operative Treatments for Total Knee Replacement Procedures,"American Academy of Orthopaedic Surgeons 2009 Annual Meeting", 6 pages, Feb. 25-28, 2008, Biowave Corporation.

Warwick, K. et al., "The Application of Implant Technology for Cybernetic Systems," *Archives of Neurology*, vol. 60:1369-1373, Oct. 2003, American Medical Association.

Wijkstrda et al., "Selective Stimulation and Blocking of Sacral Nerves: Research Setup and Preliminary Results," *Annual International Conference of the IEEE Engineering in Medicine and Biology Society*, vol. 13, No. 2, 1991.

Wilke, N. et al., "Fabrication and Characterisation of Microneedle Electrode Arrays using Wet Etch Technologies," 5 pages, Oct. 20-21, 2004, EMN04, NMRC, University College.

Zhao, M., "Genetic Analysis of Electric Signal-directed Cell Movement," 33 pages, Apr. 8, 2008, Modelling Complex Biological Systems in the Context of Genomics.

Zoll Lifecor Corporation, "What is the LifeVest Wearable Defibrillator," http://www.lifecor.com/about_lifevest/about.asp#, 1 page, printed on Jan. 7, 2011.

\* cited by examiner

Section A-A

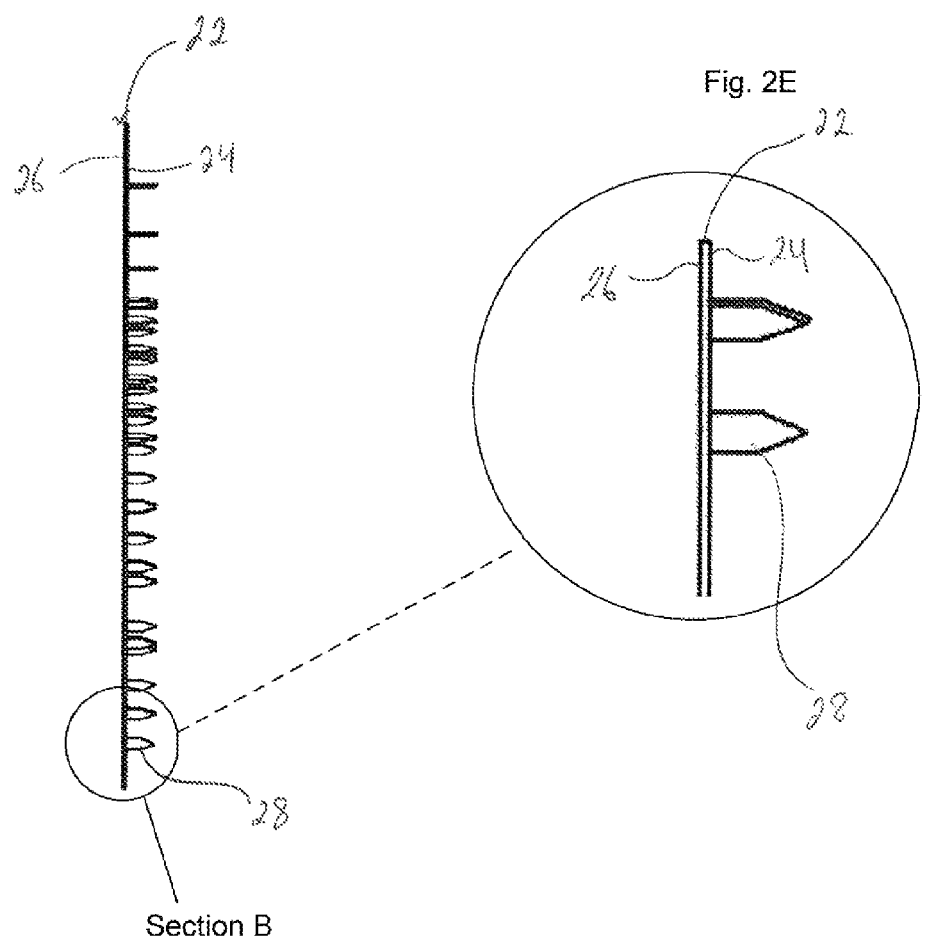

Section A

Fig. 4A
Fig. 4B
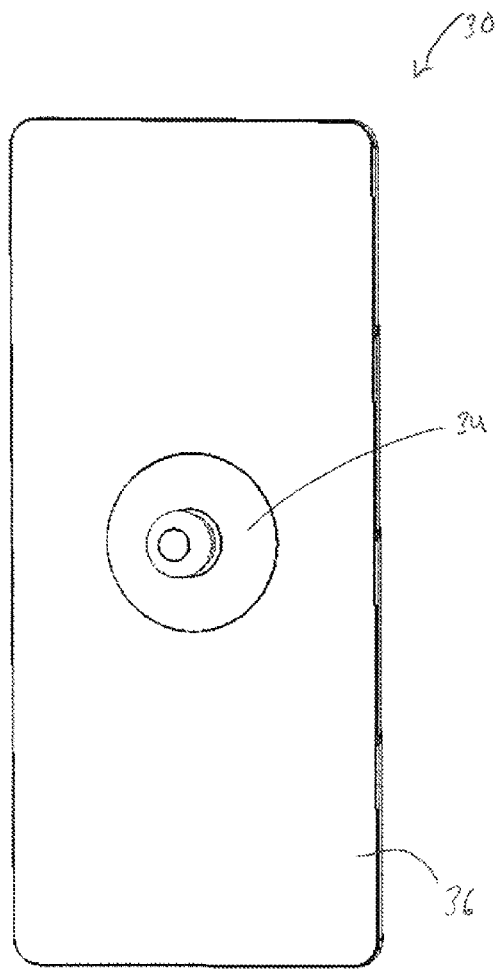
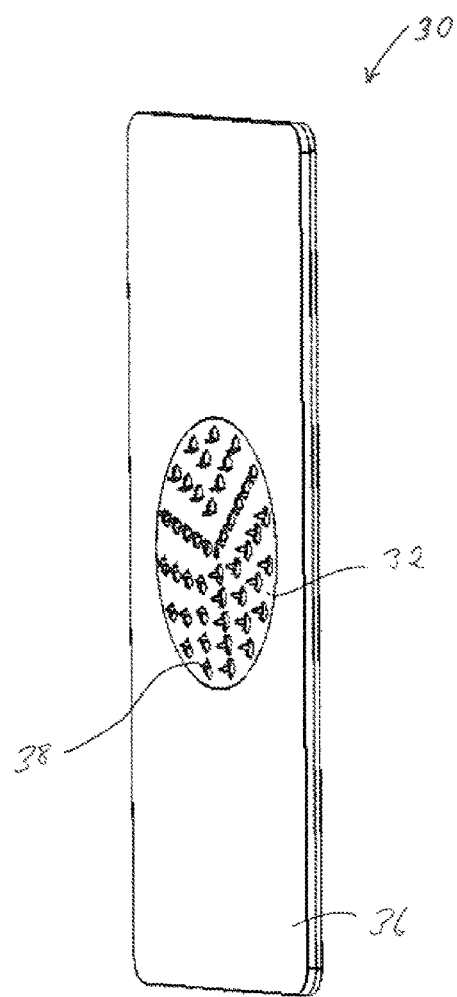

MICRONEEDLE ELECTRODE

FIELD OF THE INVENTION

The present devices and methods relate generally to microneedle electrodes having low impedance and/or resistance, which provide good electrode-tissue contact and have the ability to maintain electrical contact for an extended period of time.

BACKGROUND

Electrodes used for EKG (electrocardiogram), EEG (electroencephalogram) and EMG (electromyogram) recordings are traditionally surface electrodes and these are commonly known as standard or conventional electrodes. These conventional electrodes are either simply metal plates connected by wires or plastic discs coated with silver chloride (AgCl). A patient's skin surface requires prepping by scrubbing, e.g., with sandpaper, to remove any dead tissue, hair or any oil that might increase the resistance between the electrode surface and the tissue. The electrodes are often attached to a patient's skin using adhesive tapes. Often conductive gel is applied to the electrode surface prior to attaching to the patient's skin to improve conductivity. It is essential to have good conduction between the electrode and the patient's skin to get good electrogram recordings. The conventional electrodes have about 400Ω to 1500Ω resistance.

Microneedle electrode arrays are generally made by etching the silicon wafers (described in U.S. Pat. No. 6,256,533 by Yuzhakov et al.) and electroplating them with conductive materials like gold. This is an expensive way of making the electrodes. These are traditionally used in labs for experimental purposes only. There are even smaller scale needle arrays made (described in U.S. Pat. No. 6,334,856 by Allen et al.) for drug delivery applications, etc. There are hollow microneedle array devices (described in U.S. Pat. No. 6,603,987 by Whitson) to pierce the skin into the hypodermis layer to draw blood samples and similar devices described in U.S. Pat. No. 6,611,707 by Prausnitz et al. for the drug delivery applications.

Biowave Corporation has introduced a Percutaneous Electrode Array to be used with a Percutaneous Neuromodulation Pain Therapy System and the design of the electrode is described in U.S. Pat. Nos. 7,013,179 and 7,130,696 by Carter et al. The microneedle array is adhered to a hydrogel adhesive layer and the impedance is about 1500Ω. This electrode would not improve signal quality for EKG, EEG and EMG recordings.

A microneedle array patch is disclosed in U.S. Pat. No. 7,658,728 by Yuzhakov for a drug delivery application and the needle array is electrochemically machined and needles are bent. This device in its state can't be used for EKG, EEG and EMG recordings.

There is a need for an electrode with low impedance that provides good electrode-tissue contact with the ability to maintain that good electrical contact for an extended period of time.

BRIEF SUMMARY

Variations described herein relate to methods, systems and/or devices for enhancing conductivity of an electrical signal through a subject's or patient's skin or enhancing detection of a physiological signal in a patient or subject using one or more microneedle electrodes.

A microneedle electrode may be applied to the patient's skin by placing the microneedle electrode in direct contact with the patient's skin. The microneedles of the microneedle electrode may be inserted into the skin such that the microneedles pierce a stratum corneum of the skin up to or through a dermis of the skin. Electrical signals or physiological signals may pass or be conducted through or across the microneedle electrode and the patient's skin, where impedance of the microneedle electrode and impedance across the microneedle electrode and patient's skin is minimal and greatly reduced compared to existing technologies.

A variation of a microneedle electrode for providing enhanced conductivity of an electrical signal through a patient's skin or for enhancing physiological signal detection may include a substrate having a top surface, a bottom surface and an array of microneedles extending from the top surface. The microneedle electrode may be adapted or configured for direct contact with a patient's skin and the microneedles may pierce a stratum corneum of the skin up to or through the dermis of the skin, attaching the electrode to the skin.

In certain variations a stud may be connected to the bottom surface of the substrate by a direct mechanical and/or electrical connection. In other variations, a microneedle electrode assembly may include various components, (e.g., a substrate, a stud and/or an eyelet) each connected by direct mechanical and/or electrical connections through openings in various adhesive or other layers. The microneedle electrodes are constructed such that an electrical signal or current or physiological signal may pass through a microneedle electrode where impedance of the microneedle electrode is minimal, e.g., less than 100 ohms, providing enhanced conductivity and conductance of signals through a patient's skin.

Various methods, including methods of enhancing conductivity of an electrical signal through a subject's skin using one or more microneedle electrodes are described herein. Methods of enhancing physiological signal detection or sensing through a subject's skin using one or more microneedle electrodes are also described herein.

BRIEF DESCRIPTION OF THE SEVERAL VIEWS OF THE DRAWINGS

FIG. 2D illustrates a side view of the substrate of FIG. 2A.

FIG. 2E illustrates a magnified view of section B of the side view of the substrate of FIG. 2D.

FIG. 4A illustrates a top perspective view of a variation of a microneedle electrode assembly including a stud connected to the bottom surface of a microneedle substrate through an adhesive layer.

FIG. 4B illustrates a bottom perspective view of the microneedle electrode assembly of FIG. 4A

DETAILED DESCRIPTION

The microneedle electrodes described herein demonstrate a number of improved and unexpected properties and advantages, including, e.g.: lower impedance and/or resistance of the microneedle electrode and lower impedance and/or resistance across the microneedle electrode and skin or tissue; better anchoring or attachment of the electrode to a patient's skin; enhanced signal quality of signals detected by an electrode sensor; reduced manufacturing cost; and enhanced or improved conductance or conductivity of an electrical signal across or through the microneedle electrode and/or skin or tissue, facilitating use of the microneedle electrode as a sensor or an electrical stimulator or defibrillator. Electrical signals or current will flow easily and with greatly reduced impedance through the microneedle electrode and through a patient's skin via the microneedle electrodes described herein.

Figure 1:
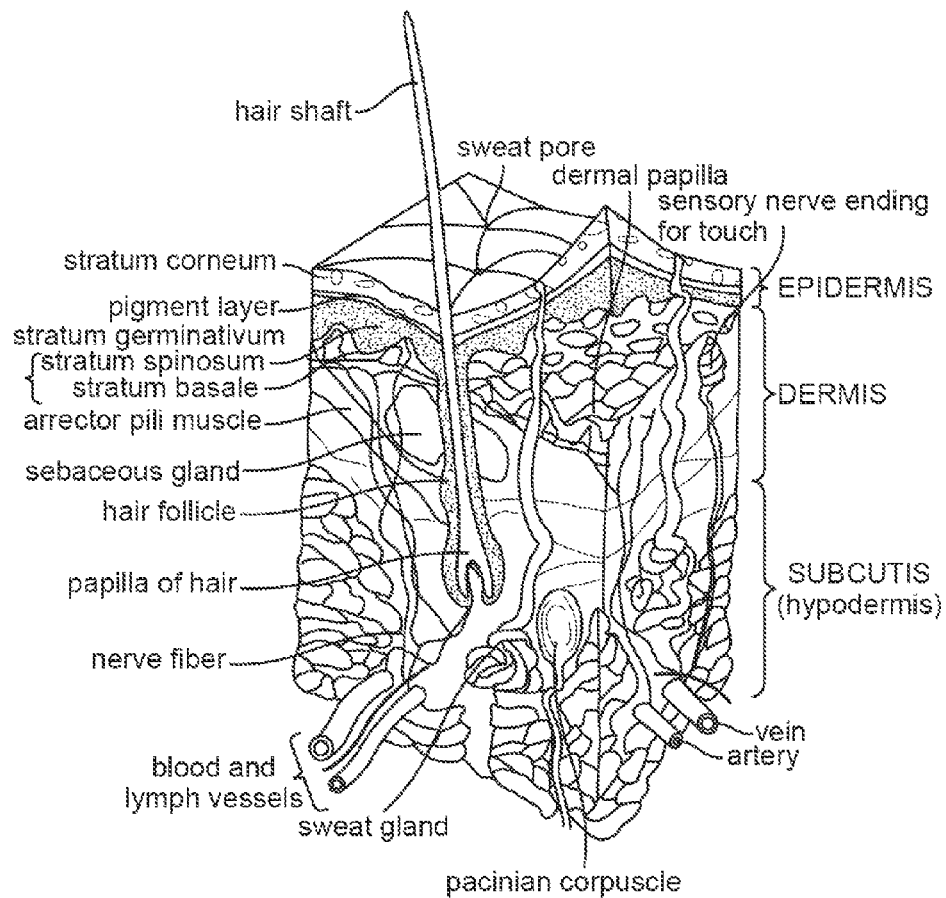
FIG. 1 illustrates a representative cross sectional view of the skin composed of an outer stratum corneum covering the epidermis and dermis of the skin and the underlying subcutaneous tissue.

FIG. 1 shows a representative cross sectional view of the skin composed of an outer stratum corneum covering the epidermis and dermis of the skin and the underlying subcutaneous tissue.

To improve or enhance conductivity or conductance or conduction of an electrical signal through a subject's or patient's skin, a microneedle electrode may be applied to a patient's skin where the microneedle electrode is placed in direct contact with a patient's skin. The microneedle electrode may be attached or anchored to the patient's skin by allowing one or more of the microneedles to pierce through the stratum corneum of the skin. The microneedles may penetrate through or across the skin, through or across the stratum corneum, through, across or up to the epidermis, up to the dermis, or optionally into or through the dermis or further into or through the skin, e.g., into the subcutis. Optionally, the microneedles may penetrate through one or more layers of the skin but not into muscle. Optionally, the microneedles are inserted in a manner that avoids or minimizes contact with certain nerves or pain nerves. As a result, the microneedle electrode may be attached or secured to the patient's skin in a minimally invasive manner with minimal or no sensation or pain caused by the microneedles, and the microneedle electrode may allow an electrical signal or current to pass through a patient's skin, bypassing or substantially bypassing the resistive stratum corneum of the skin.

Once secured to the patient's skin, an electrical signal, physiological signal or current may flow through or across the microneedle electrode, where the impedance of the microneedle electrode is less than 100 ohms or in certain embodiments, less than 10 ohms, providing improved or enhanced conductance or conductivity of signal or current flow and/or reduced impedance or resistance to signal or current flow across or through the skin and/or across or through the microneedle electrode. Components making up a microneedle electrode may be connected via direct mechanical and/or electrical connections. In certain variation, a microneedle electrode may be conductive throughout each connection between components making up the electrode, or conductive throughout at least a portion of each of the components making up the electrode. The microneedle electrode may be conductive throughout each component making up the electrode, which may allow for conductivity throughout the electrode. The microneedle electrode may provide enhanced conductivity, conductance or conduction and/or reduced impedance or resistance across or through the skin and/or across, through or in the microneedle electrode and/or between the microneedle electrode and the skin.

The microneedle electrodes described herein may be secured to a patient and made ready for recording or delivering electrical signals in half the time or less than half the time it takes to apply conventional electrodes to a patient. For example, a microneedle electrode as described herein may be secured to a patient's skin for recording or detecting electrical or physiological signals in less than five minutes. Unlike conventional electrodes, scrubbing or shaving of the patient's skin is not required to achieve the desired electrical contact or conduction between the microneedle electrode and the skin to detect or deliver electrical or physiological signals through the skin, but may be performed.

Figure 2A:
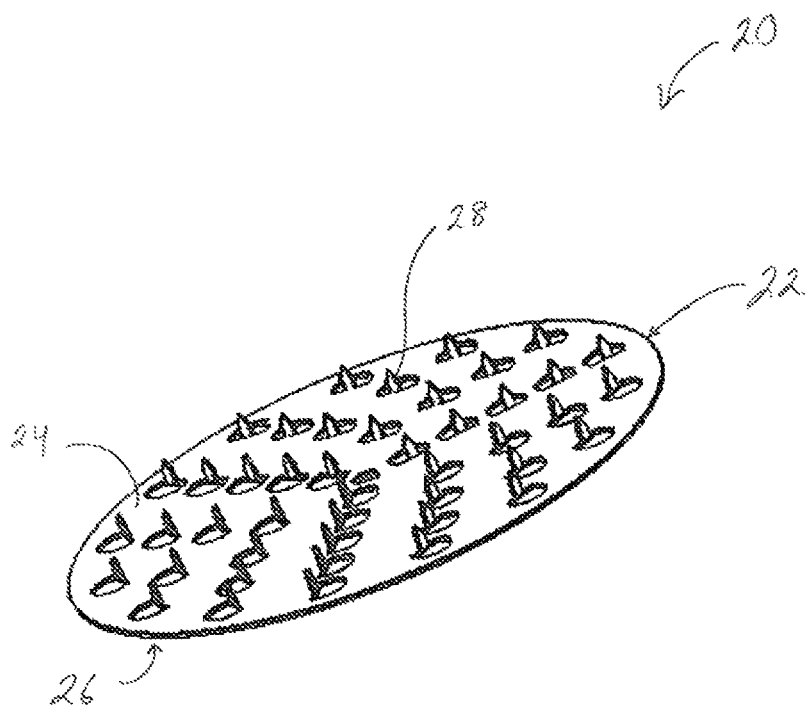
FIG. 2A illustrates a perspective view of a variation of a microneedle electrode substrate in the form of a disc.
Figure 2B:
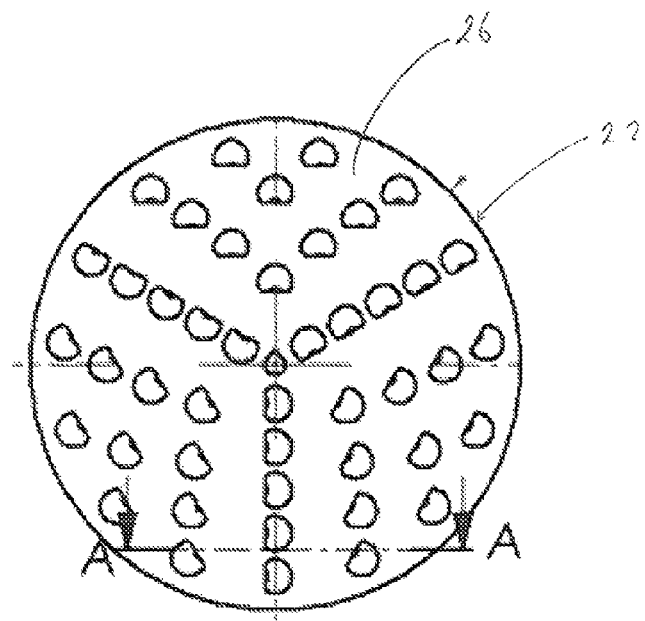
FIG. 2B illustrates a bottom view of the substrate of FIG. 2A.
Figure 2C:
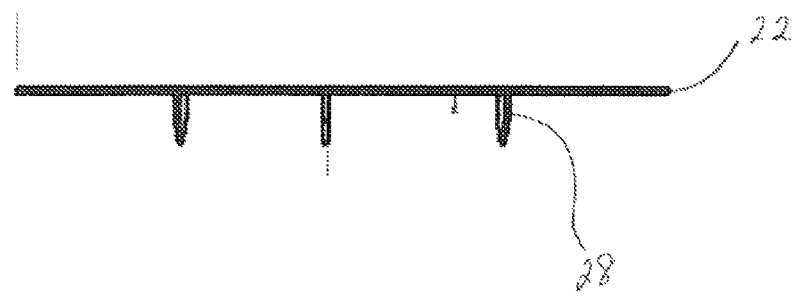
FIG. 2C illustrates a cross sectional view (section A-A) of the substrate of FIG. 2A.

Turning now to FIGS. 2A-2B, one example of a microneedle electrode 20 is illustrated as having a substrate 22 in the form of a disc. The substrate 22 includes a top surface 24 and a bottom surface 26. In one example, the disc diameter may be from, e.g., about 0.030 to about 0.100 inches, e.g., about 0.625 inches.

As shown in FIGS. 2A and 2C-2E, one or more microneedles 28 may extend from the top surface 24 of the substrate 22. The microneedles 28 may be radially distributed evenly on the substrate 22 to distribute the load evenly throughout the substrate 22. The microneedles 28 may be arranged in various patterns and number from one to as many as practicable depending upon their size, e.g., a microneedle electrode may include 45 microneedles radially distributed on the substrate 22.

In one example, the microneedles 28 may be sized to pass through the stratum corneum of the skin. The microneedles may range in length from, e.g., about 0.003 to about 0.050 inches, with a width of, e.g., about 0.005 to 0.010, and a thickness of, e.g., about 0.001 to 0.010 inches. The microneedle tip may be angled, tapered or pointed. The tip may be angled at an angle from 0 to 90° e.g., a 45° angle.

The microneedle substrate 22 may be fabricated using a variety of techniques and materials. In one variation of a technique for fabricating a substrate disc having a microneedle array, a microneedle pattern may be laid on a strip or sheet of fully hardened stainless steel material. The material may have a thickness of, e.g., 0.001 to 0.010 inches thick, e.g., about 0.003 inches. Various materials or combinations of materials may be utilized, e.g., fully hardened stainless steel such as 316L, or any stainless steel that is suitable for medical application such as 303 or 304 stainless steel or other materials having similar properties.

Figure 3A:
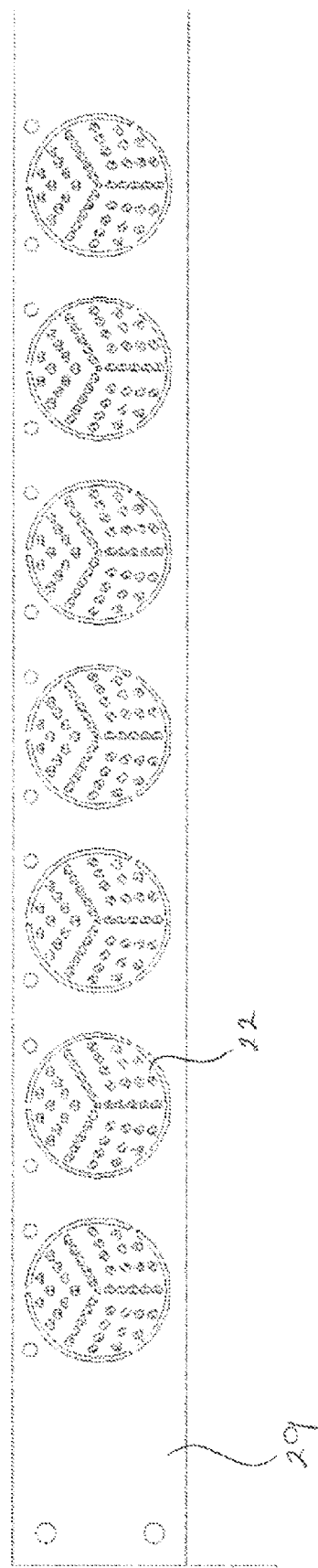
FIG. 3A illustrates one variation of a technique for fabricating a microneedle electrode substrate, where microneedle disc patterns are laid on a strip of material.

FIG. 3A illustrates one example of a technique for fabricating a microneedle electrode substrate 22, where one or more microneedle disc patterns are laid on a strip 29 of stainless steel and then photo chemically etched. The metal strip 29 may have locator holes which allow for ease of aligning the microneedle discs in a punching press/die to automate the microneedle disc fabrication process.

Figure 3B:
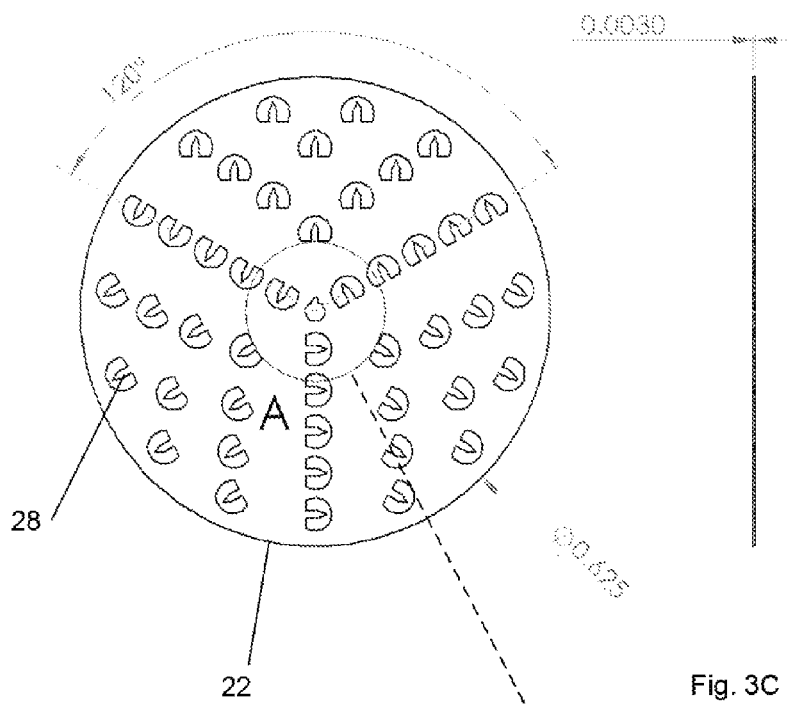
FIG. 3B illustrates a variation of a microneedle electrode substrate during fabrication having microneedles in a pre-bent configuration.
Figure 3C:
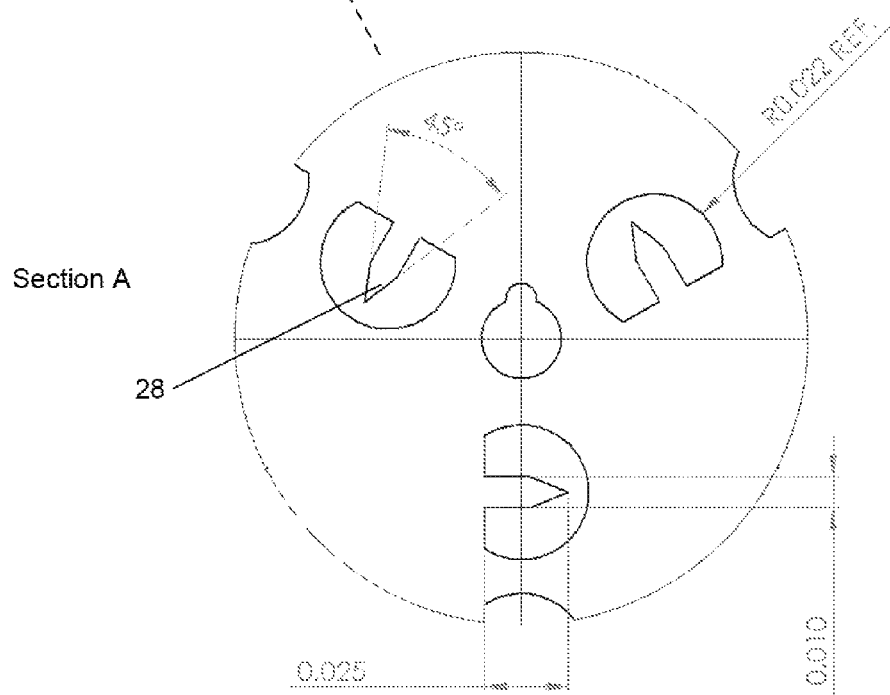
FIG. 3C illustrates a magnified view of section A of the microneedle electrode substrate of FIG. 3B.

FIGS. 3B-3C illustrate a microneedle substrate 22 where the microneedles 28 are in a pre-bent, flat configuration. During fabrication, the microneedles 28 may be bent at an angle ranging from, e.g., about 0° to 90°. For example, a microneedle may be bent using a punching die. Each microneedle substrate or disc may then be separated from the sheet or strip using a second punching die.

In another variation of a microneedle electrode, FIGS. 4A-4B illustrate a microneedle electrode assembly 30 which includes a substrate 32 having an array of microneedles 38 extending from the top surface of the substrate 32 and a stud 34 (e.g., a sensor stud) or other conductive component connected to the bottom surface of the substrate 32 by a direct mechanical and/or direct electrical connection. The assembly may include an adhesive layer 36, e.g., a gel adhesive or adhesive backed foam, and stud 34 may be attached, snapped, or pressed to the bottom surface of the substrate to form a direct mechanical and/or electrical connection between the stud 34 and substrate 32, through an opening, cutout or hole in the adhesive layer. A layer made from fabric, foam, laminate film, paper or other material may be attached to a surface of the adhesive layer 36, where the stud 34 is attached to the bottom surface of the substrate through an opening, cutout or hole in the fabric, foam, etc. layer. Optionally, the stud 34 may be welded, soldered, or otherwise directly connected to the bottom surface of the microneedle substrate 32. In one example, no or minimal conductive or nonconductive adhesive or gel is positioned on the top surface of the substrate and/or between the microneedle electrode or microneedles and the patient's skin.

Figure 5A:
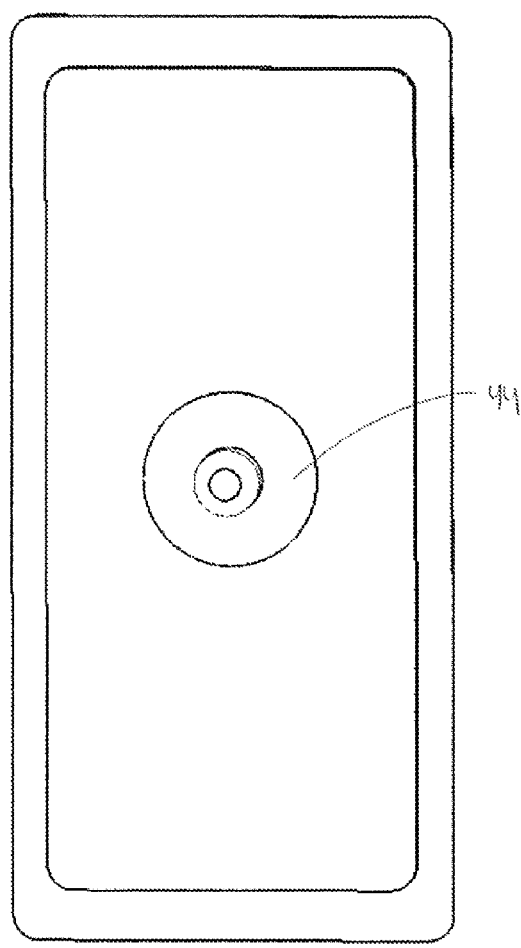
FIG. 5A illustrates a top perspective view of a variation of a microneedle electrode assembly including a stud, fabric layer, eyelet, adhesive layer, microneedle disc/substrate, and a needle protector.
Figure 5B:
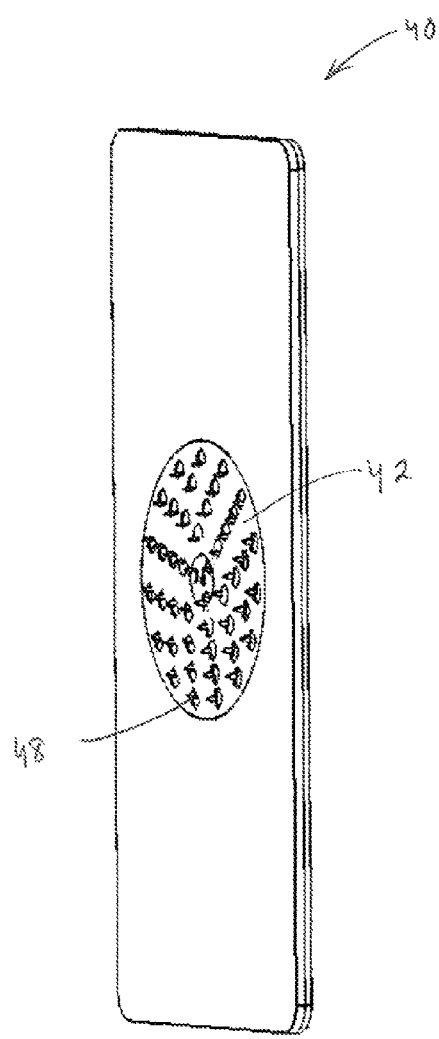
FIG. 5B illustrates a bottom perspective view of the microneedle electrode assembly of FIG. 5A
Figure 5C:
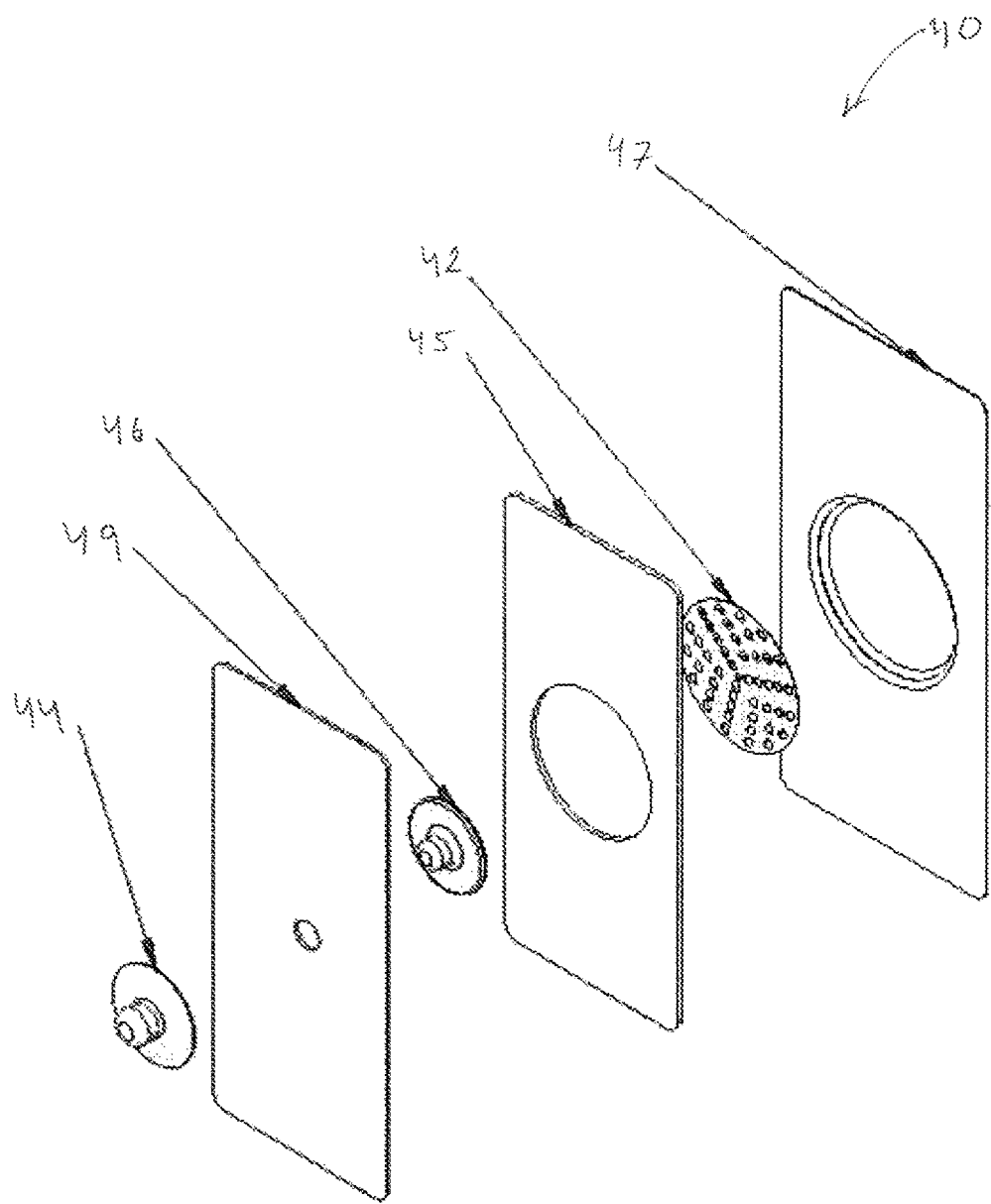
FIG. 5C illustrates an exploded perspective view of a microneedle electrode assembly according to FIGS. 5A-5B.

In another variation of a microneedle electrode assembly, as illustrated in FIGS. 5A-5C, a microneedle electrode 40 includes a stud 44 (e.g., a sensor stud) which may be attached to the bottom surface of a substrate 42 by an eyelet 46 (e.g., a sensor eyelet). An eyelet or other conductive connector or component may be used. The stud 44 and eyelet 46 are connected by a direct mechanical and/or direct electrical connection. The stud 44 and eyelet 46 may be pressed or snapped together or otherwise attached to form a strong mechanical joint and electrical connection. A layer 49 made from fabric, foam, laminate film, paper or other material may be sandwiched between stud 44 and eyelet 46. The layer may be constructed from various materials, including, e.g., Bioflex® RX754P or similar medical fabric having pressure sensitive adhesive lining. Where a layer 49 is utilized, the stud 44 is connected to the eyelet 46 through an opening, cutout or hole in the layer 49 to maintain a direct mechanical and/or direct electrical connection between stud 44 and the eyelet 46. Optionally, the stud may be welded, soldered, or otherwise directly connected to the bottom surface of the eyelet 46.

The eyelet 46 and substrate 42 may be pressed or snapped together or otherwise attached to form a strong mechanical joint and electrical connection. Optionally, the eyelet 46 may be welded, soldered, or otherwise directly connected to the bottom surface of the microneedle substrate 42 to form a strong electrical connection. Optionally, the eyelet 46 may be attached to the microneedle substrate 42 using conductive adhesive tapes, e.g., the XYZ tape 9707 from 3M™ Electronics, or through the use of a screw. The above may form a strong mechanical and/or electrical connection between the eyelet and the substrate.

Where an adhesive layer 45 is utilized, the eyelet 46 is attached to the bottom surface of the substrate 42 by a direct mechanical and/or direct electrical connection through an opening, cutout or hole in the adhesive layer 45. Also, a microneedle protector 47 made from, e.g., a thermoformed PET or similar material, may be laid over the adhesive layer 45, and the top surface of the substrate 42 and array of microneedles 48 to prevent damage to the needles 48 or unintended contact with a patient, physician or other individual handling the microneedle electrode assembly 40.

Optionally, in certain variations, a nonadhesive layer of material may be used in place of the adhesive layer, and the microneedle electrode may be adhered to skin using tape or other adhesives.

In one variation of a microneedle electrode, the stud may be connected to the substrate without an intervening layer of material positioned between the stud and substrate connection. In another variation of a microneedle electrode, the stud may be connected to the eyelet without an intervening layer of material positioned between the stud and eyelet connection. In another variation of a microneedle electrode, the eyelet may be connected to the substrate without an intervening layer of material positioned between the eyelet and substrate connection.

In certain variations, the stud to eyelet, eyelet to substrate, and/or stud to substrate connections may be a direct metal to metal (or other conductive material) connection or contact between the respective components. The components may directly contact one another, e.g., without other materials positioned between such connections. This allows for an electrical connection between the components that provides improved conductivity or conductance through or of the electrode, and the electrode may be conductive throughout.

In another variation, a microneedle electrode assembly may have one or more microneedle electrodes. Any of the variations of microneedle electrodes or microneedle electrode assemblies discussed herein may be combined or used in multiple to create a microneedle electrode assembly or patch having multiple microneedle electrodes.

Figures 6A, 6B:
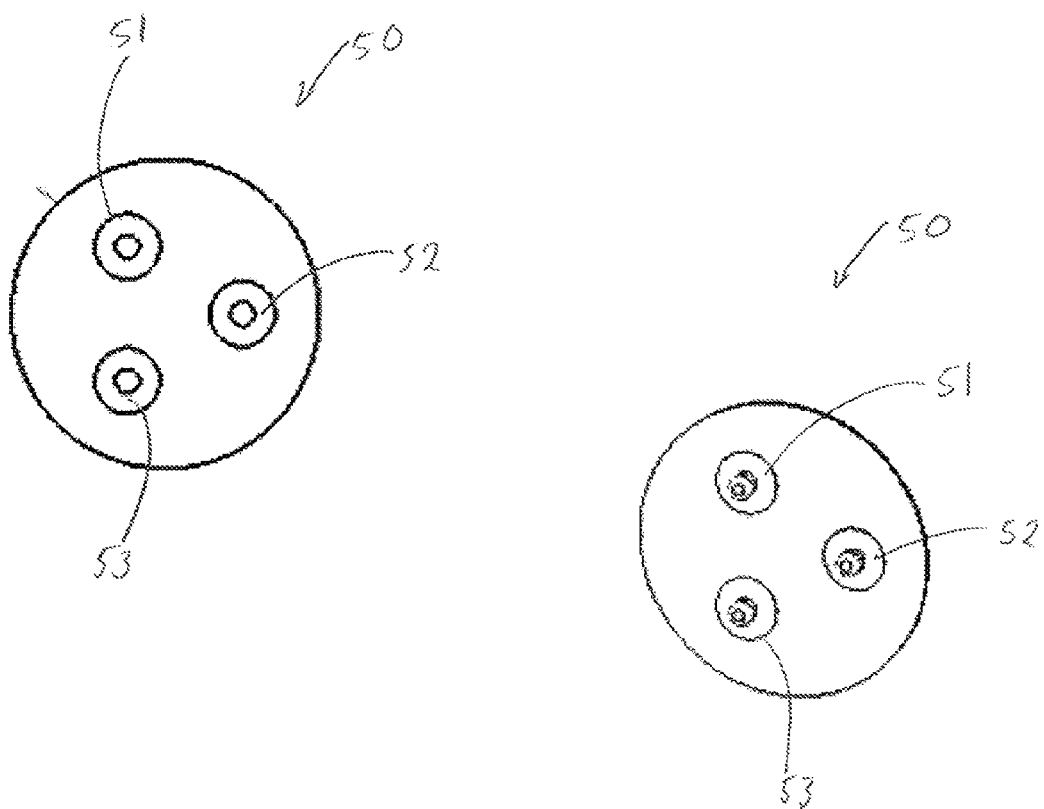
FIG. 6A illustrates a top view of a variation of a microneedle electrode assembly having multiple microneedle electrodes.
FIG. 6B illustrates a bottom view of the microneedle electrode assembly of FIG. 6A.

In one example of a microneedle electrode assembly having multiple microneedle electrodes, FIGS. 6A-6B illustrate the top and bottom surfaces of a microneedle electrode assembly 50 or patch having three microneedle electrodes. A positive electrode 51, a negative electrode 52 and a ground or neutral electrode 53.

Figure 6C:
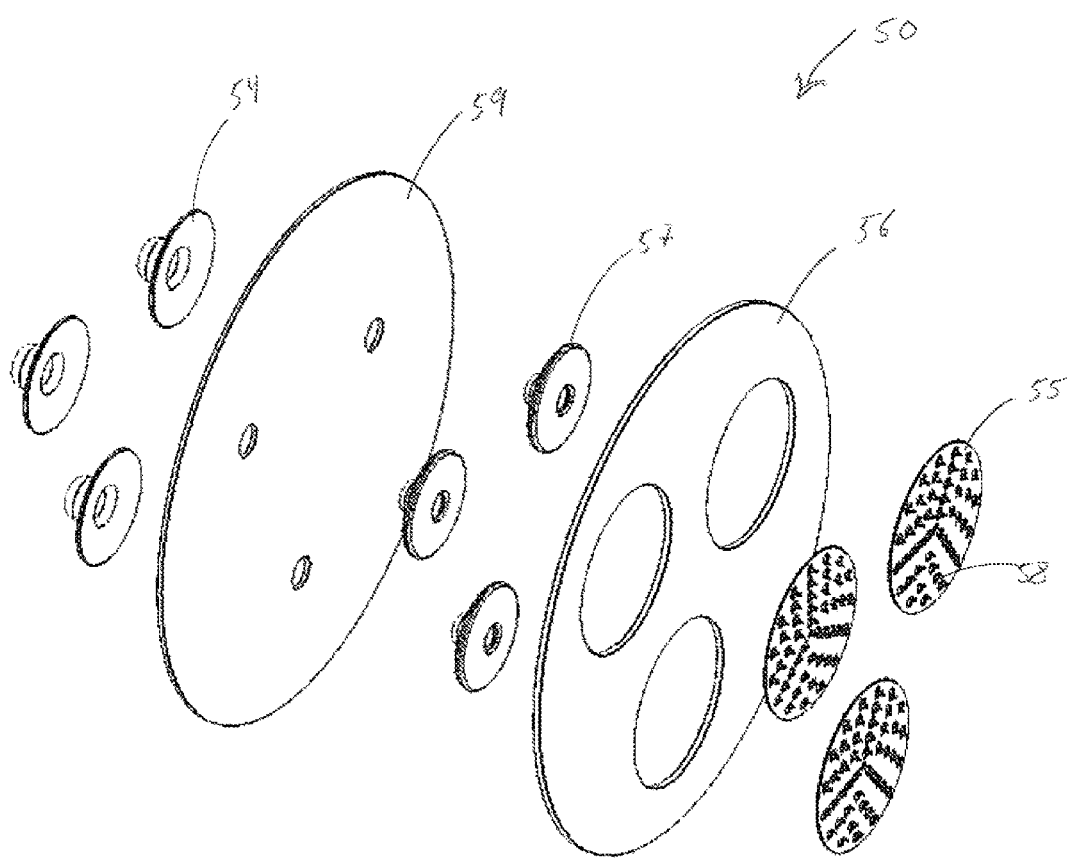
FIG. 6C illustrates an exploded perspective view of a microneedle electrode assembly according to FIGS. 6A-6B.
Figure 7A:
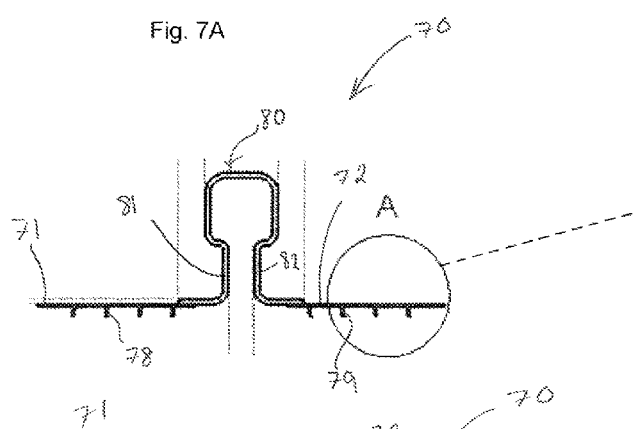
FIGS. 7A-7D illustrate various views of a variation of a microneedle electrode having two microneedle substrates facing in opposite directions and connected to one another by a tab.
Figure 7B:
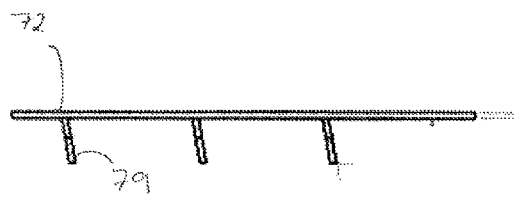
Figure 7C:
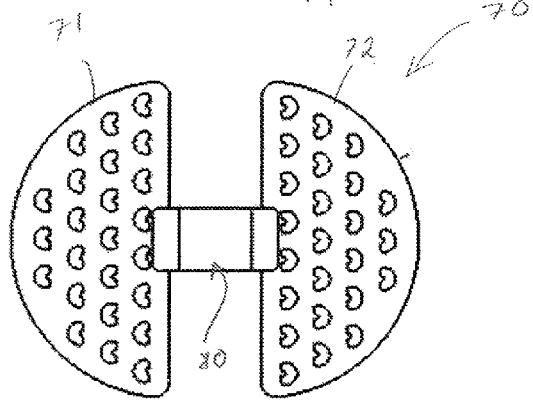
Figure 7D:
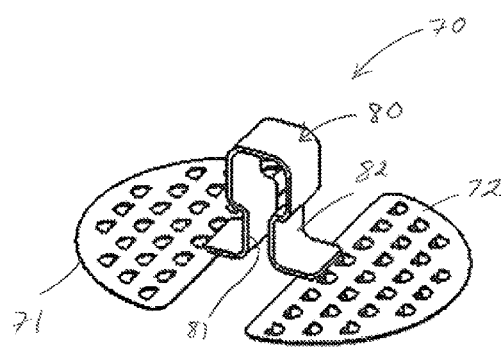

As shown in FIG. 6C, the microneedle electrode assembly 50 includes a stud 54 (e.g., sensor stud) attached to the bottom surface of a substrate 55 by an eyelet 57 (e.g., sensor eyelet). The stud 54 is attached to the eyelet 57 through an opening, cutout or hole in a layer 59 made from fabric, foam, laminate film, paper or other material to maintain a direct mechanical and/or direct electrical connection between the stud 54 and the eyelet 57. The eyelet 57 is attached to the bottom surface of the substrate 55 through an opening, cutout or hole in the adhesive layer 56 to maintain a direct mechanical and/or direct electrical connection between the eyelet 57 and the substrate 55. Optionally, a microneedle protector 60 may be laid over the adhesive layer 56, and the top surface of the substrate 55 and array of microneedles 58, to prevent damage to the needles or unintended contact with a patient, physician or other individual handling the microneedle electrode assembly 50.

The three microneedle electrodes 51, 52, 53 may be electrically isolated from each other. Indeed, the microneedle electrodes may be separated a sufficient distance from each other so as to minimize or avoid electrical conduction between the electrodes or electrical conduction from one electrode to another. This distance between electrodes may vary depending on the particular patient to which the microneedle electrode assembly is attached. The distance between electrodes may vary depending on the size of the patient and the size of the patient's body parts. For example, the distance may vary depending on the patient's foot size and anatomy. Typically the distance is about 3 cms and in some patients this distance could be as high as 6 cms. One or more of each of a positive, negative and ground electrode may be utilized in a microneedle electrode assembly or patch.

Various materials and components may be utilized to construct a microneedle electrode or microneedle electrode assembly according to the variations described herein. In one example, a microneedle electrode may include a sensor stud and a sensor eyelet. The sensor stud may be NO159-BA-X and the sensor eyelet may be NO133-SF-X from Newark, Inc. The sensor stud and sensor eyelet may be made from stainless steel. A fabric, foam or paper layer, e.g., Bioflex® RX754P or similar medical fabric having pressure sensitive adhesive lining, may be sandwiched between the sensor stud and sensor eyelet. A gel adhesive or adhesive backed foam layer having a window cutout for a formed microneedle disc may be positioned or laid over the fabric layer on the sensor eyelet side of the fabric layer surface. The gel adhesive layer may be, e.g., AG603 from AmGel Technologies or single coated polyethylene foam like 2932P from Tyco.

A microneedle substrate or disc may be welded to the sensor eyelet, soldered onto the sensor eyelet, attached to the sensor eyelet using conductive adhesive tapes, or attached to the sensor eyelet using a screw. A thermoformed needle protector made from PET or similar material is positioned or laid on the gel adhesive layer and over the microneedle substrate and microneedle array to minimize or prevent needle damage or unintended contact with an individual handling or wearing the microneedle electrode assembly.

Various designs and configurations of the components may be utilized in the microneedle assemblies described herein. For example, the fabric, foam, paper, etc. layer and the gel adhesive layer may have the same width and/or length. The needle protector may be slightly wider and/or longer than the fabric, foam, paper layer and/or adhesive layer to allow a user to grab the needle protector and peel the adhesive layer to expose the microneedle electrode.

In certain variations, it is important to have minimal, low or no resistance or impedance across the stud, eyelet, and/or microneedle substrate. For example, the resistance or impedance of or across the stud, eyelet, and/or microneedle substrate may be less than 200Ω or less than 100Ω or less than 50Ω or less than 10Ω. For example resistance or impedance across a stud and microneedle substrate may be less than 200Ω. The stud and eyelet may be pressed together to form a strong direct mechanical joint and/or direct electrical connection where the resistance or impedance of the stud and eyelet is less than 50Ω.

In other variations, resistance or impedance of the stud and eyelet or the stud and eyelet connection may be less than 10Ω or less than 1Ω. Resistance or impedance of the eyelet and substrate or eyelet and substrate connection may be less than 10Ω or less than 1Ω. Resistance or impedance of the stud and substrate or stud and substrate connection may be less than 10Ω or less than 1Ω. Resistance or impedance of the microneedle electrode may be less than 10Ω or less than 5Ω or less than 1Ω (ohms).

In another variation of a microneedle electrode, FIGS. 7A-7D illustrate a microneedle electrode having two split microneedle substrates facing in opposite directions and connected to one another by a tab. The microneedle electrode 70 includes a first substrate 71 and a second substrate 72, the substrates each having a top surface, a bottom surface and an array of microneedles 78, 79 extending from the top surfaces of the substrates 71, 72. The first and second substrates 71, 72 face in opposite directions such that the array of microneedles 78 on the first substrate 71 are angled in a direction opposite the array of microneedles 79 on the second substrate 72. The microneedle electrode 70 also includes a tab 80 having a first leg 81 connected to the bottom surface of the first substrate 71 and a second leg 82 connected to the bottom surface of the second substrate 72. The connection between the tab 80 and the first and second substrates 71, 72 may be a direct mechanical and/or direct electrical connection. The tab may be mechanically fastened, welded, soldered, or otherwise directly connected to the bottom surface of the substrate 42.

The first and second legs 81, 82 of the tab 80 can be pressed together to force the first and second substrates 71, 72 together prior to inserting the microneedle arrays 78, 79 into a patient's skin. The first and second legs 81, 82 may then be released to allow the first and second substrates 71, 72 to spread apart thereby forcing the angled microneedles 78, 79 on the first and second substrates 71, 72 into the stratum corneum of the skin up to or through a dermis of the skin, and securing the microneedle electrode 70 to the patient's skin. When the microneedle electrode 70 is attached to the patient's skin, an electrical signal or current may pass through the microneedle electrode 70 and across the patient's skin where impedance or resistance of the microneedle electrode is less than 10 ohms.

In other variations, one or more microneedle substrates or discs may be utilized which are connected to one or more tabs.

In use, the tab 80 of the microneedle electrode is pressed, forcing the first and second legs 81, 82 of the tab 80 together and forcing the first and second substrates 71, 72 together. The microneedle electrode 70 is placed over or on the skin and the tab 80 is then released, thereby forcing the first and second legs 81, 82 and the first and second substrates 71, 72 apart, which forces the angled microneedles 78, 79 on the first and second substrates 71, 72 into the stratum corneum of the skin up to a dermis of the skin.

In certain variations, a user may grab the connecting tabs, squeeze the tabs, place the electrode on the patient's skin surface and release it. Needles may be oriented in opposing directions allowing the needles to move in opposite directions upon the release of the tab, thus grabbing on to the patient's skin surface easily. The microneedles may be positioned at a slight angle. In certain variations, the microneedles may not be perpendicular to the disc surface. Typically the microneedles have an angle of about 80°. The angle may vary anywhere from 40° to 85°. The disc shape can vary. The tab's width is typically about 0.145" and it can vary anywhere from 0.08" to 0.25". Typical height of the tab is about 0.25" and it can vary anywhere from 0.125" to 0.75". Typical thickness of the tab is about 0.010" and it can vary from 0.005" to 0.075". The thicker the tab, the greater force required to squeeze the tab to bring the electrode substrates or discs together.

In another variation of a microneedle electrode, the tab may act like a spring. The first and second legs of the tab may be flexed together, moving the first and second substrates or discs together prior to microneedle array insertion into a patient's skin. The microneedle electrode is placed over or on the patient's skin and upon release of the flexed first and second legs, the tension stored in the legs forces the first and second substrates apart, forcing the angled microneedles on the first and second substrates into a stratum corneum of the skin up to or through the dermis of the skin. As a result, the microneedle electrode may be secured or attached to the patient's skin.

In another variation, the tab may be fabricated from various shape memory materials or alloys, e.g., nickel-titanium alloys such as Nitinol. The tab may be contractable to force the first and second plates together and expandable to force the first and second plates apart, such that the angled microneedles can be inserted into a stratum corneum of the skin up to or through the dermis of the skin. This mechanism would facilitate the securing of the microneedle electrode to the patient's skin.

In any of the above variations, the tab may be connected to a lead wire via an alligator clip or other attachment or clip. Optionally, fabric or paper layers, adhesive layers and/or needle protectors may be assembled into these microneedle electrode variations as described in the designs and embodiments described above.

Figure 8:
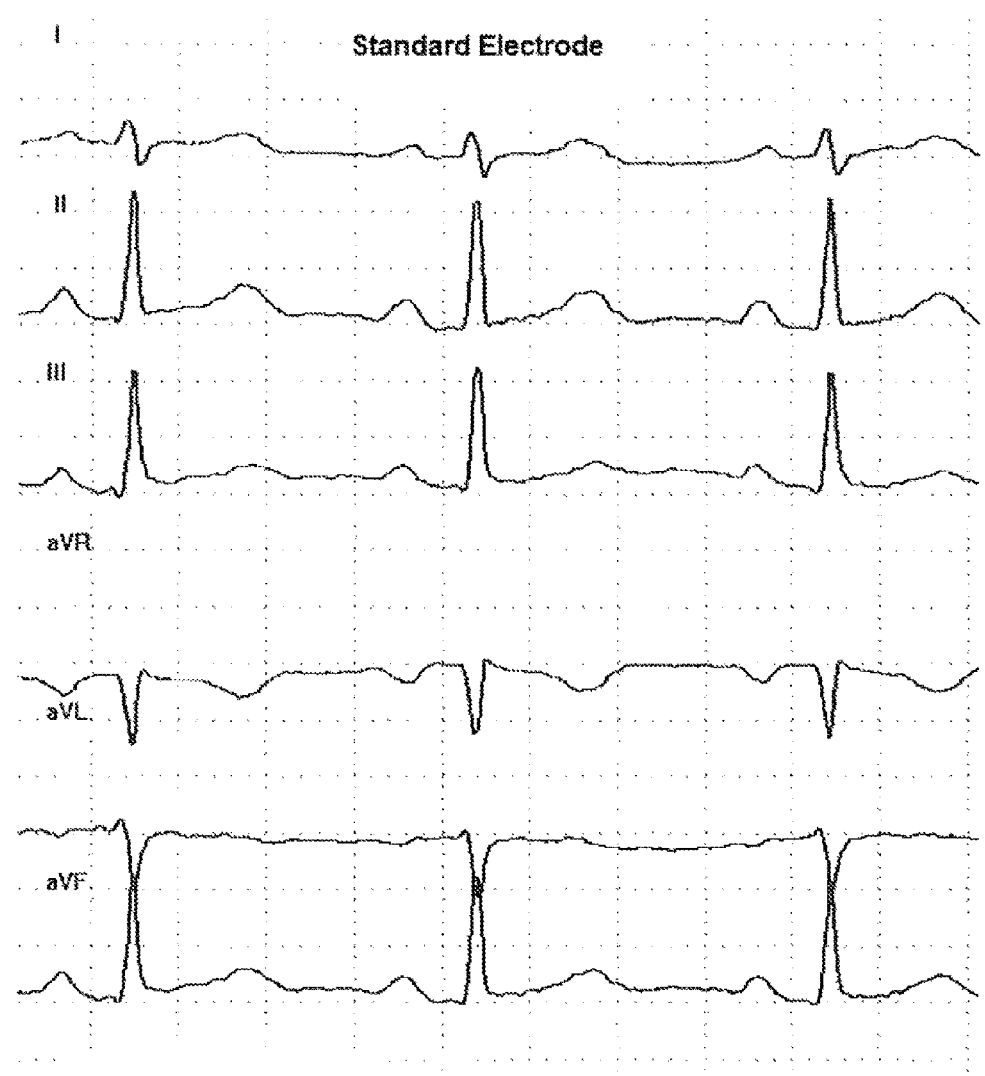
FIG. 8 illustrates an exemplary EKG recording of and individual using a standard electrode.
Figure 9:
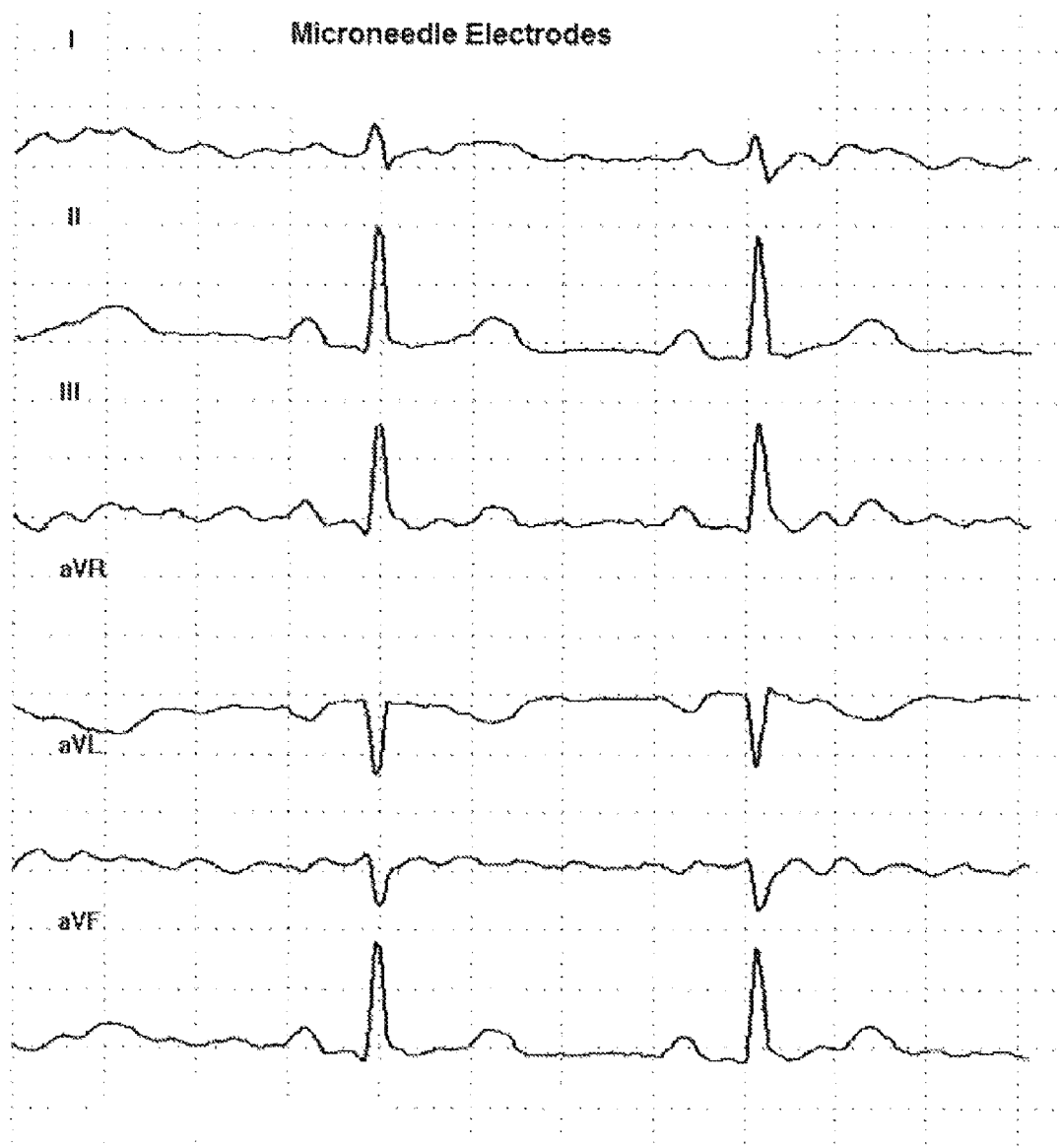
FIG. 9 illustrates an exemplary EKG recording of the same individual as in FIG. 8, using a variation of a microneedle electrode as described herein.

As further evidence of the unexpected and improved conductance or conductivity and reduced impedance or resistance properties of the microneedle electrodes and microneedle electrode assemblies described herein, FIGS. 8 and 9 provide exemplary EKG recordings for standard electrodes compared to exemplary EKG recordings for microneedle electrodes as described herein.

FIG. 8 illustrates an exemplary EKG recording of an individual using standard non-microneedle electrodes of the type known to persons having ordinary skill in the art. The electrodes were applied to the skin of the individual, the surface of which was prepared by scrubbing with sand paper and alcohol wipes.

In contrast, FIG. 9 illustrates an exemplary EKG recording of the same individual using a microneedle electrode according to the variations of microneedle electrodes described herein. The microneedle electrode was applied to the skin of the individual without any skin surface preparation. A comparison of the two recordings clearly reveals the enhanced signal quality of the EKG recording illustrated in FIG. 9.

Typically it takes about 15 to 20 minutes to place six (6) standard electrodes on a patient to perform an EKG recording. However, the same number the microneedles can be placed in less than the half of the time it takes to place the standard surface electrodes because, scrubbing or shaving is not necessary. The EKG signals recorded using the microneedle electrodes as described in the variations and embodiments described herein are cleaner or contain less noise and amplitude of the signals can be 10% to 30% higher, e.g., as shown in FIG. 9.

In certain variations, a microneedle substrate or disc typical thickness is about 0.003". The thickness may vary any where from 0.001" to 0.005". Typical diameter of a microneedle disc is about 0.625". The diameter may vary anywhere from 0.500" to 3.000". Typically, the microneedle height is about 0.023". The height may vary from 0.005" to 0.075". The number of microneedles per disc depends on the diameter of the disc or the surface area. Typically there are about 140 to 150 needles per square inch area. This can vary anywhere from 100 to 300 needles per square inch area. Typically the needles are bent perpendicular to the disc surface. This angle could be anywhere from 75° to 120°. The needle tip may be tapered and may be sharp like a "needle point". Typically the needle taper angle is about 45°. This can vary from 2° to 60°. Electrodes can be of any shape i.e. round, rectangular, trapezoidal, triangular, or any regular or irregular shape.

Typical material used for the microneedle electrodes, the tab and the other components making up the electrodes or electrode assemblies include stainless steal, e.g., 316L stainless steel. Other materials like 300 series or 400 series stainless steels, gold, silver, platinum, titanium, nitinol, metal or any other conductive biocompatible materials can be used to fabricate the electrodes and/or microneedles.

Various arrangements and numbers of microneedles may be utilized as practicable and are contemplated herein. The above arrangements, materials, and dimensions for the microneedle electrodes described herein are exemplary and are not intended to be limiting.

In use one or more microneedle electrodes as described herein may be applied to a patient's skin to enhance or improve conductivity or conductance of an electrical signal through a patient's skin. A method of enhancing conductivity of an electrical signal through a subject's skin using a microneedle electrode may also be provided. The microneedle electrode may be placed in direct contact with the patient's skin. The microneedles may be inserted into the patient's skin such that one or more microneedles pierce or penetrate the stratum corneum of the skin up to or through the dermis of the skin. The microneedle electrode grips the skin and secures the microneedle electrode to the patient's skin. Optionally, an adhesive may be used to secure the microneedle electrode to the skin. Once secured to the patient's skin, signals, electrical signals or current passes through the microneedle electrode where impedance or resistance of the microneedle electrode is less than 10 ohms.

The microneedle electrode may be placed in direct contact with the patient's skin, e.g., without a conductive gel or a hydrogel adhesive layer or other adhesive positioned between the microneedle electrode or microneedles and the patient's skin, or positioned on the electrode or on the skin. Impedance of the microneedle electrode may be less than 100 ohms or less than 10 ohms and/or impedance across or between the microneedle electrode and the patient's skin may be less than about 350 ohms. Optionally, a conductive gel or adhesive layer could be utilized on the skin or electrode in certain variations.

In one variation, the microneedle electrode is applied to a patient's skin as a sensor for recording electrical and/or physiological signals in a patient's body. For example, electrical signals, current and/or voltage may be conducted, transmitted, passed or detected through or across the microneedle electrode. In another variation, the microneedle electrode is applied to a patient's skin and maintains good electrode to tissue electrical contact between the microneedle electrode and the patient's skin in a manner sufficient for detecting or recording various signals in a patient's body, e.g., for performing EKG, EEG, ECG and/or EMG recordings.

In another variation, a method of enhancing or improving physiological signal detection or sensing through a subject's skin using a microneedle electrode is provided. A microneedle electrode is applied to the subject's skin by placing the microneedle electrode in direct contact with the subject's skin. The microneedles of the microneedle electrode are inserted into the skin such that the microneedles pierce stratum corneum of the skin up to or through dermis of the skin or further. One or more physiological signals are detected through the microneedle electrode where impedance of the microneedle electrode is less than 10 ohms.

In yet another variation, the microneedle electrode may function as a defibrillator where the microneedle electrode is configured to conduct, pass, transmit or deliver electrical current and/or voltage through the microneedle electrode and into a patient's body to provide sufficient stimulation to a patient depending on their condition. The low impedance microneedle electrodes described herein are ideal for use in defibrillation because they have decreased current requirements making them less painful, easier to use, and less dangerous to surrounding personal when utilized. Such microneedle electrodes may also be utilized for temporary external pacing.

For example, the microneedle electrode may be used with a wearable defibrillator, such as the LifeVest® wearable cardioverter defibrillator manufactured by ZOLL Lifecor® Corporation which is worn outside the body. The microneedle electrode may be used as a dry, non-adhesive or adhesive sensing electrode to continuously monitor the patient's heart to detect abnormal heart rhythms. Optionally, the microneedle electrode may be used in the same device as a therapy electrode for delivering an electrical shock to restore normal rhythm, e.g., in an emergency setting.

In certain variations, the microneedle electrodes described herein may be utilized in combination with an injectable electrically conductive gel to stimulate a predetermined body part or record electrical signals in the body. The microneedle electrodes may be used in systems for stimulation of nerves and body parts, e.g., systems utilizing multiple waveforms. For example; the microneedle electrodes described herein may be used in place of or in combination with the electrodes used in the systems and methods described in the U.S. Pat. No. 7,647,112; US Pub. No. 2005/0277998; and US Pub. No. 2009/0132018, each of which is incorporated herein by reference in their entirety.

In certain variations, the microneedle electrodes described herein may be used to simulate a nerve, muscle or body part of an individual, e.g., by delivering an electrical or electromagnetic signal or stimulation to the individual or for delivering therapeutic electrical or electromagnetic energy to a treatment site on a subject. In other variations, the microneedle electrodes may be used for detecting or sensing an electrical signal, physiological signal, muscle stimulation or twitching in a subject or patient's body part. For example, the electrodes may be used to monitor physiological signals in an individual or to monitor or deliver electrical or electromagnetic stimulation of an individual. For example, the microneedle electrodes may be used in the systems and methods described in US Pub. No. 2008/0306325 and U.S. application Ser. No. 12/508,529, each of which is incorporated herein by reference in their entirety.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. A method of enhancing conductivity of an electrical signal through a subject's skin using a microneedle electrode comprising:
    applying a microneedle electrode to the subject's skin by placing microneedles of the microneedle electrode in direct contact with the subject's skin;
    inserting the microneedles of the microneedle electrode into the skin such that the microneedles pierce stratum corneum of the skin up to dermis of the skin; and
    allowing an electrical signal to pass through the microneedle electrode where impedance of the microneedle electrode is less than 10 ohms, wherein the microneedle electrode comprises a conductive metal substrate having microneedles extending therefrom which is formed by etching or cutting a microneedle pattern into a sheet of conductive metal and bending the microneedles to a desired angle.

2. The method of claim 1, wherein the microneedle electrode is placed in direct contact with the subject's skin without a conductive gel positioned between the microneedle electrode and the subject's skin and where impedance across the microneedle electrode and the subject's skin is less than 350 ohms.

3. The method of claim 1, wherein inserting the microneedles into the subject's skin secures the microneedle electrode to the subject's skin.

4. The method of claim 1, further comprising securing the microneedle electrode to the subject's skin with an adhesive.

5. The method of claim 1, further comprising recording an electrical physiological signal of a subject's body via the microneedle electrode.

6. The method of claim 5, further comprising maintaining electrode to tissue electrical contact between the microneedle electrode and the subject's skin in a manner sufficient for performing EKG, ECG, EEG, or EMG recordings.

7. The method of claim 1, wherein the microneedle electrode comprises a stud and a substrate with an array of microneedles extending therefrom, wherein the stud is attached to a bottom surface of the substrate by a direct electrical connection allowing for conductivity throughout the electrode.

8. The method of claim 7, wherein the microneedle electrode further comprises an eyelet, wherein the stud is attached to the eyelet by a direct mechanical and electrical connection and the eyelet is attached to a bottom surface of the substrate by a direct electrical connection allowing for conductivity throughout the electrode.

9. The method of claim 1, wherein the conductive metal substrate having microneedles extending therefrom is a stainless steel substrate.

10. The method of claim 1, wherein the conductive metal substrate having microneedles extending therefrom is formed by chemical etching a microneedle pattern into a strip of conductive metal and bending the microneedles to an angle of ninety degrees.

11. The method of claim 1, wherein a conductive gel is not positioned between the microneedles and the subject's skin.

12. A microneedle electrode for providing enhanced conductivity of an electrical signal through a subject's skin comprising:
a conductive metal substrate having a top surface, a bottom surface and an array of microneedles extending from the top surface which is formed by etching or cutting a microneedle pattern into a sheet of conductive metal and bending the microneedles to a desired angle, wherein the microneedle electrode is adapted for direct contact between the microneedles and a subject's skin and configured to pierce stratum corneum of the skin up to dermis of the skin; and
a stud connected to the bottom surface of the substrate by a direct electrical connection allowing for conductivity throughout the electrode, wherein the microneedle electrode is configured to allow an electrical signal to pass through the microneedle electrode and impedance of the microneedle electrode is less than 10 ohms.

13. The microneedle electrode of claim 12, further comprising an adhesive layer, wherein the stud is attached to the bottom surface of the substrate by a direct electrical connection through an opening in the adhesive layer.

14. The microneedle electrode of claim 12, wherein no conductive gel or adhesive is positioned on the top surface of the substrate or between the microneedles and the subject's skin.

15. The microneedle electrode of claim 12, wherein the stud is connected to the substrate by an eyelet.

16. The microneedle electrode of claim 15, wherein the stud and eyelet are pressed together to form a strong mechanical joint and electrical connection.

17. The microneedle electrode of claim 15, further comprising a fabric layer, wherein the stud and eyelet have a direct mechanical and electrical connection through an opening in the fabric layer.

18. The microneedle electrode of claim 15, further comprising a foam layer, wherein the stud and eyelet have a direct mechanical and electrical connection through an opening in the foam layer.

19. The microneedle electrode of claim 15, wherein the eyelet and substrate are pressed together to form a strong mechanical joint and electrical connection.

20. The microneedle electrode of claim 15, wherein the eyelet and substrate are connected by welding, soldering or by using conductive adhesives to form a strong electrical connection.

21. The microneedle electrode of claim 12, wherein the microneedle electrode is a sensor configured to record physiological signals in a subject's body.

22. The microneedle electrode of claim 12, wherein the microneedle electrode is a defibrillator configured to transmit electrical current and voltage into a subject's body.

23. The microneedle electrode of claim 12, wherein the stud is connected to the substrate by an eyelet without an intervening layer of material positioned between the stud and eyelet connection.

24. The method of claim 12, wherein the conductive metal substrate having a top surface, a bottom surface and an array of microneedles extending from the top surface is a stainless steel substrate.

25. A method of enhancing physiological signal detection through a subject's skin using a microneedle electrode comprising:
applying a microneedle electrode to the subject's skin by placing microneedles of the microneedle electrode in direct contact with the subject's skin;
inserting the microneedles of the microneedle electrode into the skin such that the microneedles pierce stratum corneum of the skin up to dermis of the skin; and
detecting a physiological signal through the microneedle electrode where impedance of the microneedle electrode is less than 10 ohms, wherein the microneedle electrode comprises a conductive metal substrate having microneedles extending therefrom which is formed by etching or cutting a microneedle pattern into a sheet of conductive metal and bending the microneedles to a desired angle.

* * * * *